US011103235B2

(12) United States Patent
Sauer, MD et al.

(10) Patent No.: US 11,103,235 B2
(45) Date of Patent: Aug. 31, 2021

(54) ROTATION ADAPTER AND RECEIVER FOR MINIMALLY INVASIVE SURGICAL DEVICES

(71) Applicant: LSI Solutions, Inc., Victor, NY (US)

(72) Inventors: Jude S. Sauer, MD, Pittsford, NY (US); Jason C. Patti, Rochester, NY (US)

(73) Assignee: LSI Solutions, Inc., Victor, NY (US)

( * ) Notice: Subject to any disclaimer, the term of this patent is extended or adjusted under 35 U.S.C. 154(b) by 230 days.

(21) Appl. No.: 15/980,776

(22) Filed: May 16, 2018

(65) Prior Publication Data

US 2018/0256159 A1    Sep. 13, 2018

Related U.S. Application Data

(60) Division of application No. 15/242,073, filed on Aug. 19, 2016, now Pat. No. 10,939,904, which is a
(Continued)

(51) Int. Cl.
*A61B 17/04* (2006.01)
*F16H 25/18* (2006.01)
(Continued)

(52) U.S. Cl.
CPC ....... *A61B 17/0469* (2013.01); *F16H 25/186* (2013.01); *A61B 17/0401* (2013.01);
(Continued)

(58) Field of Classification Search
CPC ........ B23B 51/12; B23B 51/14; B23B 31/00; B23B 45/00; A61B 2017/0488;
(Continued)

(56) References Cited

U.S. PATENT DOCUMENTS 5,520,702 A    5/1996 Sauer
5,762,256 A *  6/1998 Mastri ............... A61B 17/0684
                                                    227/176.1
(Continued)

FOREIGN PATENT DOCUMENTS

CA         2582964        9/2007
DE     202013104656      12/2013
(Continued)

OTHER PUBLICATIONS

Young, Lee W.; Feb. 9, 2017 International Search Report; PCT—Written Opinion of the International Searching Authority in corresponding International Application No. PCT/US2016/047839.
(Continued)

*Primary Examiner* — Sarah W Aleman
(74) *Attorney, Agent, or Firm* — Michael E. Coyne; Christopher B. Miller

(57) ABSTRACT

A rotation adapter for a minimally invasive surgical apparatus is disclosed. The rotation adapter has a proximal journal and a distal journal. The rotation adapter also has a rotation index coupled between the proximal and distal journals. The rotation adapter further has an actuator input and an effector output. A rotation adapter receiver for a minimally invasive surgical apparatus is also disclosed. The rotation adapter receiver has opposing beams and a proximal bushing coupled between the opposing beams. The rotation adapter receiver also has a distal bushing coupled between the opposing beams. The rotation adapter receiver further has a rotation constraint coupled between the opposing beams and positioned between the proximal and distal bushings.

9 Claims, 36 Drawing Sheets

Related U.S. Application Data continuation-in-part of application No. 14/325,824, filed on Jul. 8, 2014, now Pat. No. 10,603,027.

(60) Provisional application No. 62/207,287, filed on Aug. 19, 2015.

(51) Int. Cl.

| | | |
|---|---|---|
| A61B 17/06 | (2006.01) | |
| A61B 17/062 | (2006.01) | |
| A61B 17/00 | (2006.01) | |
| A61B 90/00 | (2016.01) | |

(52) U.S. Cl.
CPC ....... *A61B 17/0467* (2013.01); *A61B 17/0482* (2013.01); *A61B 17/0483* (2013.01); *A61B 17/0487* (2013.01); *A61B 17/0625* (2013.01); *A61B 90/08* (2016.02); *A61B 2017/00398* (2013.01); *A61B 2017/00455* (2013.01); *A61B 2017/042* (2013.01); *A61B 2017/0409* (2013.01); *A61B 2017/0445* (2013.01); *A61B 2017/0454* (2013.01); *A61B 2017/0488* (2013.01); *A61B 2017/06042* (2013.01); *A61B 2090/0811* (2016.02)

(58) Field of Classification Search
CPC .......... A61B 2017/0409; A61B 17/221; A61B 17/0469; A61B 17/0483; A61B 17/320758; A61B 17/0482; A61B 17/0487
See application file for complete search history.

(56) References Cited

U.S. PATENT DOCUMENTS

| | | |
|---|---|---|
| 5,797,538 A | 8/1998 | Heaton et al. |
| 6,283,670 B1 | 9/2001 | Blankinship |
| 6,733,218 B2 | 5/2004 | Del Rio |
| 7,235,086 B2 | 6/2007 | Sauer |
| 7,344,545 B2 | 3/2008 | Takemoto et al. |
| 7,435,251 B2 | 10/2008 | Green |
| 8,313,496 B2 | 11/2012 | Sauer |
| 2003/0060841 A1 | 3/2003 | Del Rio et al. |
| 2005/0135890 A1* | 6/2005 | Bauman ................ B23B 31/008 408/239 R |
| 2006/0027978 A1* | 2/2006 | Young ................ B23B 31/1238 279/62 |
| 2008/0012245 A1* | 1/2008 | Peters .................... B23B 51/12 279/5 |
| 2010/0089974 A1 | 4/2010 | Shelton |
| 2011/0040308 A1 | 2/2011 | Cabrera et al. |
| 2011/0233927 A1 | 9/2011 | Ramon |
| 2015/0045819 A1 | 2/2015 | Houser et al. |
| 2015/0084336 A1 | 3/2015 | Brown |

FOREIGN PATENT DOCUMENTS

| | | |
|---|---|---|
| EP | 0650007 | 10/1993 |
| EP | 1946708 | 7/2008 |

OTHER PUBLICATIONS

Feb. 21, 2019 Extended European Search Report; Franz, Volker, Extended European Search Report for EP 16837923.

* cited by examiner

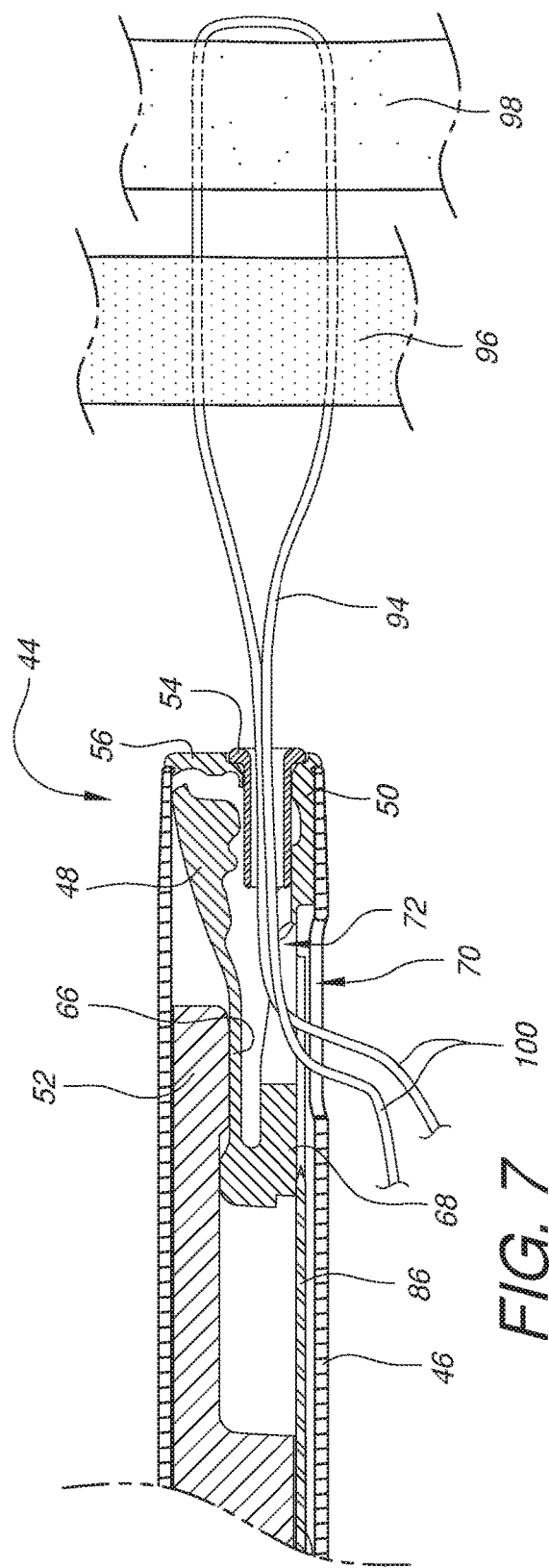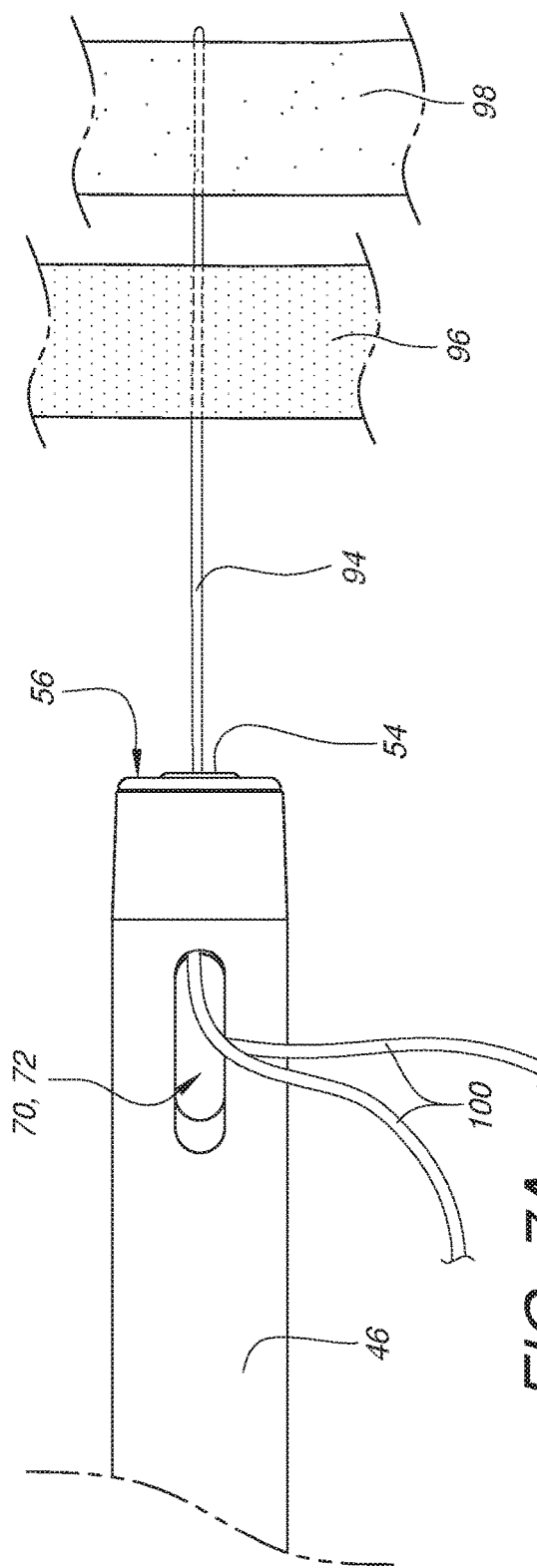

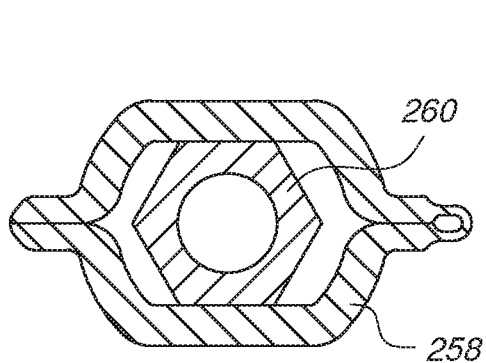 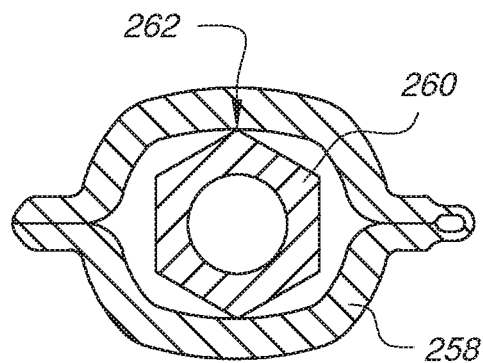
FIG. 22A          FIG. 22B
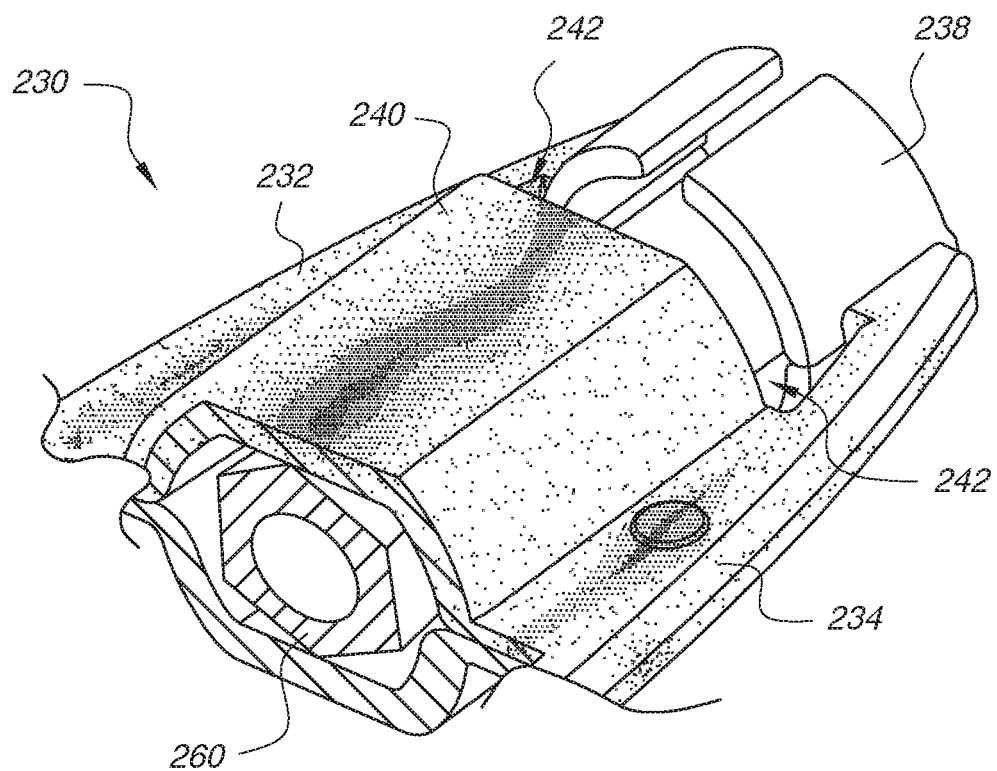
FIG. 23

ROTATION ADAPTER AND RECEIVER FOR MINIMALLY INVASIVE SURGICAL DEVICES

CROSS REFERENCE TO RELATED APPLICATIONS

This patent application is a divisional of U.S. patent application Ser. No. 15/242,073 filed Aug. 19, 2016 and entitled "ROTATION ADAPTER AND RECEIVER FOR MINIMALLY INVASIVE SURGICAL DEVICES". U.S. patent application Ser. No. 15/242,073 is a continuation-in-part of U.S. patent application Ser. No. 14/325,824 filed Jul. 8, 2014 and entitled "CRIMPING INSTRUMENT WITH REDUCED DIMENSION, CONTINUED COMPATIBILITY, AND TISSUE PROTECTION FEATURES". The Ser. Nos. 15/242,073 and 14/325,824 applications are hereby incorporated by reference in their entirety.

FIELD

The claimed invention relates generally to minimally invasive surgical instruments, and more particularly to a rotation adapter and receiver which enable effective rotation of an end effector on such minimally invasive surgical devices.

BACKGROUND

Malleable suture fasteners such as the sleeves sold under the trademarks TiKNOT® and COR-KNOT® by LSI Solutions, Inc. are a significant improvement over hand or instrument-tied knots in laparoscopic surgical procedures. The sleeves, which are made of a malleable material that has proven safe with prolonged exposure to body tissue, are slid over two or more strands of suture and deformed or crimped to secure the strands of suture.

An exemplary crimping instrument is shown in U.S. Pat. No. 7,235,086, entitled "CRIMPING INSTRUMENT WITH MOTION LIMITING FEATURE", assigned to LSI Solutions, Inc., of Victor, N.Y. FIG. 1 illustrates such a crimping device 20, having a handle 22 with an actuator 24 that is movable relative to the handle 22. A hollow shaft 26 extends from the handle 22 to a distal end 28 of the shaft 26. The distal end 28 of the shaft 26 can be seen more clearly in the partial cross-sectional view of FIG. 1A.

Suture ends 30 can be threaded through a crimping sleeve 32 held between a hammer 34 and an anvil 36. The suture ends 30 pass out a hole in the side of the shaft 26, and the device can be used to position the crimping sleeve 32 at a desired location on the suture 31 relative to a surface 38 through which the suture 31 has been secured (for example, tissue, a replacement anatomical structure such as a heart valve, or an augmentive anatomical structure such as a heart valve annulus).

Squeezing the actuator 24 towards the handle 22 causes a wedge 40, located in the shaft 26, to advance and to force the hammer 34 into the crimping sleeve 32. The hammer 34 crimps the crimping sleeve 32 against the anvil 36, and the suture 31 is held tightly by the deformed sleeve 32. A blade 42 may also be incorporated within the shaft 26 and can be simultaneously moveable by the actuator 24 in order to trim the suture ends 30.

Such instruments for attaching suture fasteners 32 have proven to be very effective. The Ti-KNOT® and COR-KNOT® devices from LSI Solutions, Inc. (information available at www.lsisolutions.com) have been widely accepted by surgeons for the recognized benefits of time savings, ease of use, and reliability. (See, for example, "New Knot Tying Technique for Minimally Invasive Approach to Mitral Valve Repair", an abstract by Rodriguez, Sutter, and Ferdinand presented at the AATS 2011 Mitral Conclave in New York, N.Y. in 2011 or "Use of Automatic Knot-Tying and Cutting Device is Shortening Aortic Cross-Clamp Times in Minimally Invasive Mitral Valve Surgery", an abstract by Gersak and Robic presented at the 26th Annual EACTS Meeting in Barcelona, Spain in 2012.)

Devices like the COR-KNOT® device enable many types of minimally invasive surgery (MIS), or, more specifically, minimally invasive cardiac surgery (MICS). MIS is a type of surgery performed through one or more small incisions or access sites created in a patient. MIS has been shown to have at least equivalent morbidity and mortality outcomes as compared to conventional approaches, with reported advantages of reduced postsurgical pain, better respiratory function, shorter hospital stay, and improved cosmesis. Such advantages are increased with ever smaller sized MIS access points. As a result, it is very desirable to have smaller and smaller MIS tools which can enable the use of such smaller MIS access points. In other MIS approaches, specifically, for example MICS for aortic valve replacement, a smaller device tip, especially with more rounded edges, would be easier to position remotely and would reduce the potential for device-related tissue trauma and/or prosthetic damage.

The outside of the prosthetic valve shall be close in size to the space available at the aortic root. The larger a replacement aortic valve's blood passage area is relative to the opening in the outflow track of the left ventricle, the more blood can pass through without flow disturbances. After removing the diseased native valve, it is therefore desirable to install a replacement prosthetic valve with the largest possible diameter into the aortic root. Replacement heart valves usually have a sewing ring attached to and just peripheral to the valve leaflet. This ring is typically several millimeters wide, is designed to be sutured to the aortic root, and can then be secured in place with mechanical knots. Given the narrow space available over the sewing ring between the valve leaflets and the aortic root, a mechanical knot delivery device about the same size as the radial width of a sewing ring is desired. A narrower MICS device tip would enable less challenging placement of the mechanical knot into this narrow space as well as easier device tip positioning and removal. A narrow device tip can also enable the use of larger diameter valves for improved blood flow.

Unfortunately, it is not a simple matter to reduce the size of all of the components in a device such as the current COR-KNOT® device because such changes could also impact the size (and therefore the operating properties) of the mechanical crimping sleeve 32. Devices such as the COR-KNOT® device are always put through rigorous testing and qualification procedures, both internally with the manufacturer and externally, such as when obtaining Food and Drug Administration (FDA) and European Community (CE mark) clearance. Currently, the outside diameter of the COR-KNOT® device shaft 26 is approximately two-hundred thousandths of an inch. The inside diameter of the shaft 26 is approximately one hundred seventy-six thousandths of an inch, while the titanium sleeve 32 has an outside diameter of approximately forty-nine thousandths of an inch. Subtracting the room needed for the sleeve 32 within the shaft 26, this means that the current COR-KNOT® device only has about one hundred twenty-seven thousandths of an inch to accommodate the hammer 34, anvil 36, travel space for the wedge 40, and various associated tolerances. Reducing the size of the crimpable sleeve to gain more room in a smaller shaft could potentially require a different size crimpable sleeve. The current sleeve has been very successfully used in over 250,000 patients throughout the world. This sleeve size has proven completely reliable and useful with a broad range of common surgical sutures; no failures have been reported after securing over 1.8 million sutures. This sleeve size is remarkably effective and well-received; changing its dimensions or configuration would have the potential to render it less efficacious. Likewise, it would be unwise to change the operating features of the hammer 34 and anvil 36 which impart the reliable crimped configuration for the proven suture sleeve 32. Still, it would be desirable to have a crimping device 20 with smaller shaft 26 dimensions in order to enable use with ever smaller MIS access points and in MICS applications.

Therefore, there is a need for a surgical crimping instrument having smaller dimensions when compared to the currently available devices, which are already quite small. Furthermore, there is a need for such a reduced dimension surgical crimping instrument to have continued compatibility with existing uncrimped sleeves for loading and crimping them to an identical configuration to ensure the continuation of reliability and performance from such proven sleeves. There is a need for such devices to place a premium on patient safety, so it would also be desirable for this surgical crimping instrument to have even further enhanced tissue protection features. Finally, it is highly desirable for the minimally invasive surgical apparatuses of all types (including, but not limited to, surgical crimping instruments and surgical suturing devices) to have an ability for the end effector to rotate independently from the handle/actuator so that more ergonomic and flexible use is possible for surgeons.

SUMMARY

A rotation adapter for a minimally invasive surgical apparatus is disclosed. The rotation adapter has a proximal journal and a distal journal. The rotation adapter also has a rotation index coupled between the proximal and distal journals. The rotation adapter further has an actuator input and an effector output.

A rotation adapter receiver for a minimally invasive surgical apparatus is also disclosed. The rotation adapter receiver has opposing beams and a proximal bushing coupled between the opposing beams. The rotation adapter receiver also has a distal bushing coupled between the opposing beams. The rotation adapter receiver further has a rotation constraint coupled between the opposing beams and positioned between the proximal and distal bushings.

BRIEF DESCRIPTION OF THE DRAWINGS

FIG. 7 is a partial cross-sectional side view of the embodied instrument for crimping a suture fastener from FIG. 2 with suture ends passed through a crimpable sleeve on one end of the instrument and exiting through a slot in the bottom of the instrument.

FIG. 7A is a bottom view of the embodied instrument for crimping a suture fastener from FIG. 7.

FIGS. 22A and 22B illustrate a schematic cross-sectional view of a rotation constraint interacting with a rotation index in both a resting state and a transitory state between two resting positions, respectively.

FIG. 23 illustrates stresses on a rotation adapter receiver and shows how the stresses are, in part, alleviated by a beam of the rotation adapter receiver.

Figure 1:
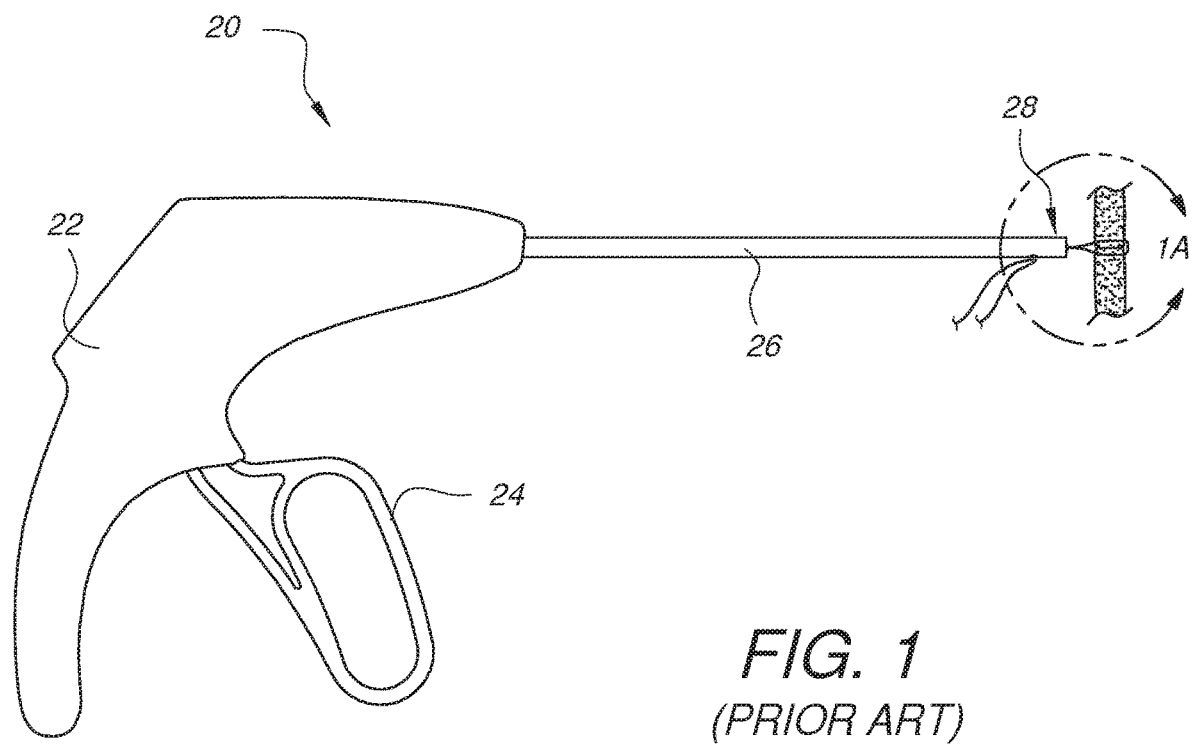
FIG. 1 illustrates a prior art surgical crimping instrument for crimping a suture fastener to one or more sutures.
Figure 1A:
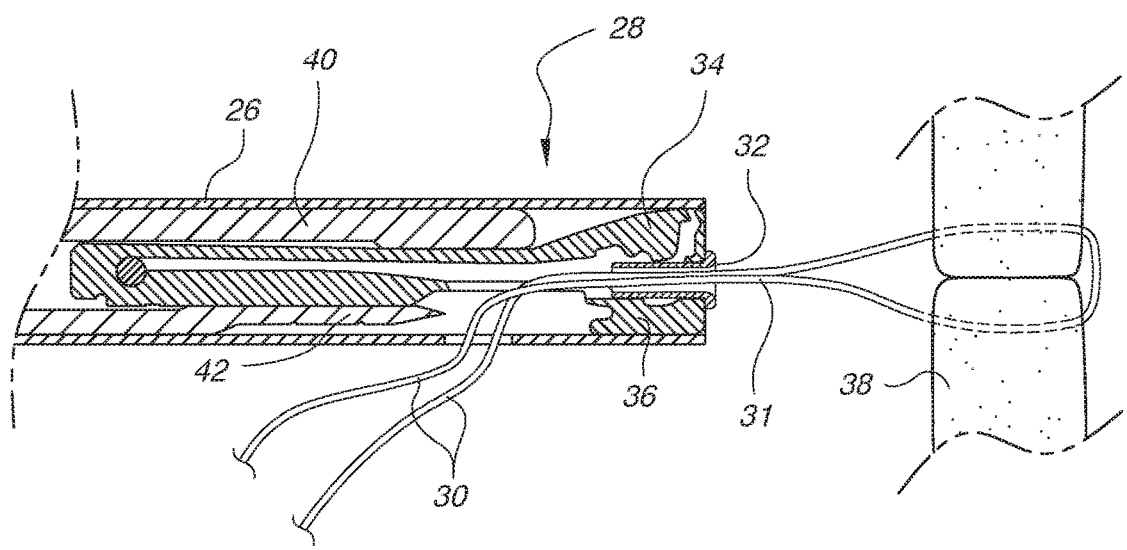
FIG. 1A shows an enlarged partial cross-sectional view of the distal end of the shaft of the prior art surgical crimping instrument of FIG. 1.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 2:
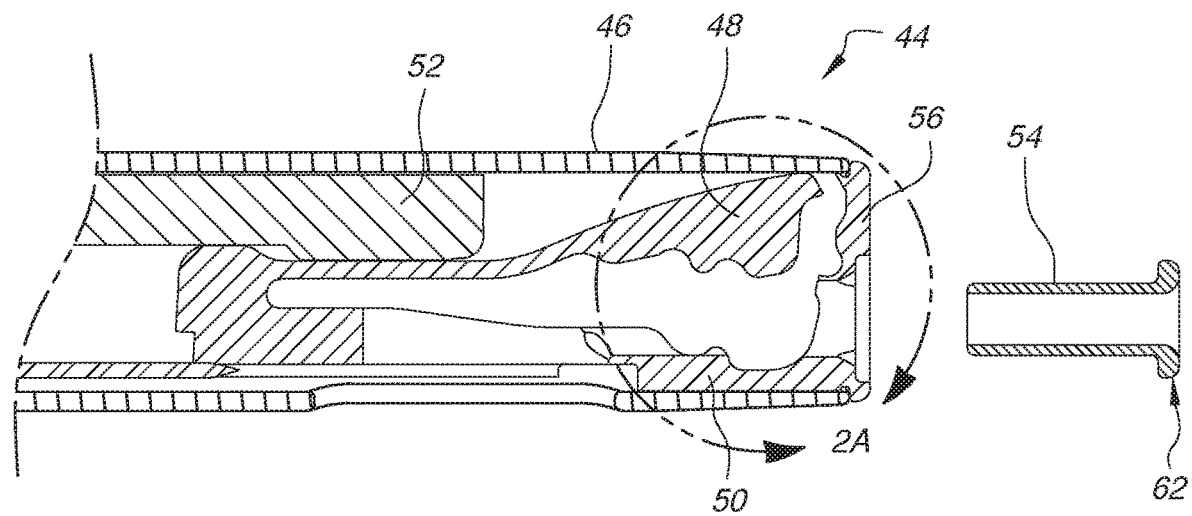
FIG. 2 illustrates, in cross-sectional view, the distal end of a new embodiment of an instrument for crimping a suture fastener to a surgical suture, the instrument enabling reduced dimensions when compared to the prior art while being backwards compatible with existing, FDA approved crimpable sleeves. A crimpable sleeve is not yet installed in the instrument shown in FIG. 2.

FIG. 2 illustrates, in cross-sectional view, the distal end 44 of one embodiment of an instrument for crimping a suture fastener to a surgical suture. It should be understood that the term "suture", as used herein, is intended to cover any thread, cable, wire, filament, strand, line, yarn, gut, or similar structure, whether natural and/or synthetic, in monofilament, composite filament, or multifilament form (whether braided, woven, twisted, or otherwise held together), as well as equivalents, substitutions, combinations, and pluralities thereof for such materials and structures. The distal end 44 includes a shaft 46 which houses some of the instrument components, including a hammer 48, and anvil 50, and a pusher 52. The hammer 48 is movable relative to the anvil 50 for crimping a suture fastener 54 therebetween. In this view, the suture fastener 54 is not yet installed in the device. However, in later views, the suture fastener 54 will be installed and the operation of the hammer 48 and the anvil 50 will be discussed in more detail. Generally, however, the pusher 52 is moveable in a direction substantially parallel to a longitudinal axis of the shaft 46 and is configured to engage at least one of the hammer 48 and the anvil 50 for urging the hammer 48 and anvil 50 together.

Figure 2A:
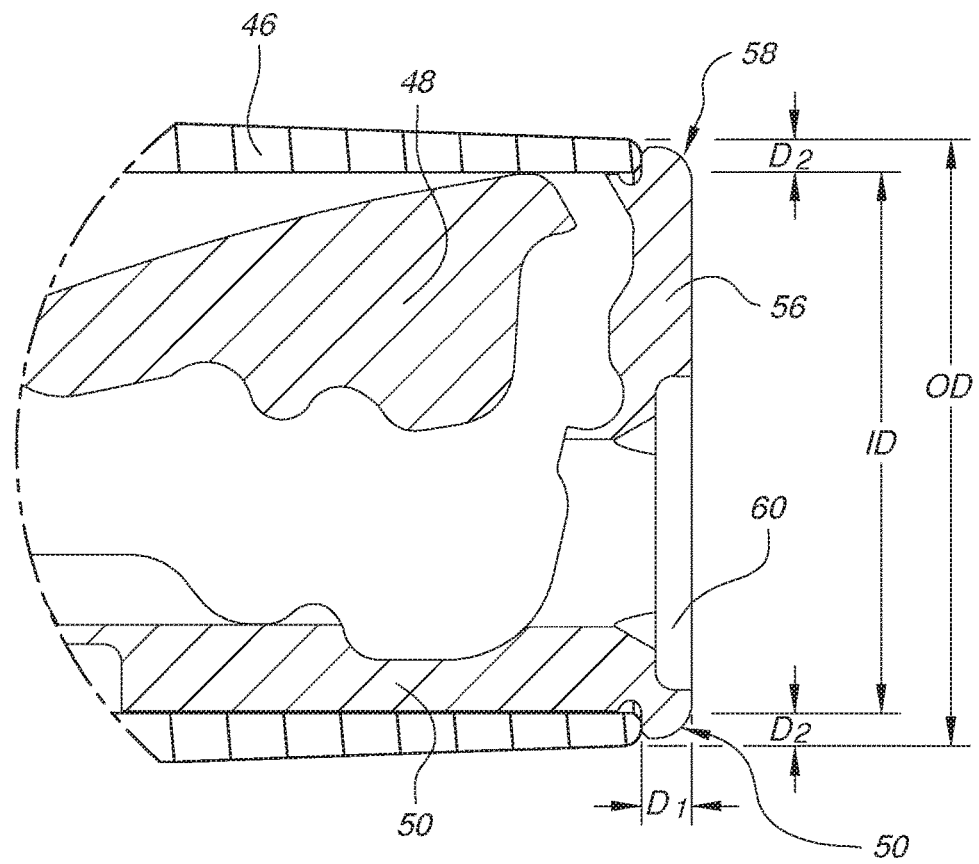
FIG. 2A shows an enlarged cross-sectional view of the distal end of the shaft of the instrument from FIG. 2.

The crimping instrument also includes an expanded receiving face 56 configured to receive the suture fastener 54. The expanded receiving face 56 can be seen in more detail in the enlarged cross-sectional view of FIG. 2A. Unlike the prior art where the receiving face is flush with the end of the shaft, in the claimed invention, the expanded receiving face 56 sticks out a longitudinal distance $D_1$ past the end of the shaft 46. In some embodiments, the expanded receiving face 56 is also sized to reach beyond the inside diameter (ID) of the shaft 46 and outward towards, to, or beyond the outside diameter (OD). For example, the expanded receiving face 56 in the embodiment of FIG. 2A expands radially a distance $D_2$ past the inner diameter (ID) towards the outside diameter (OD). Depending on the embodiment, a rounded edge 58 can be formed on the expanded receiving face 56 at least partially within the expansion distances $D_1$ and $D_2$. This rounded edge 58 of the expanded receiving face 56 can provide one measure of tissue protection when the tip of the instrument is brought into contact with a patient. This can be especially important in light of the small dimensions involved in the construction of such a small minimally invasive device. In the prior art device, where the receiving face was flush with the end of the shaft, minimal corner rounding could be provided in the shaft due to the thinness of the shaft wall. As the size of the device is reduced, and the shaft wall is potentially made even thinner, there is just not enough thickness in the wall for adequate rounding. The expanded receiving face 56 provides a solution to this problem by allowing a rounded surface 58 to be formed which can protect tissue from the potentially sharp edges of the shaft 46.

Despite these advantages of the expanded receiving face 56, it was still counterintuitive to expand the receiving face from the previous design because it would have meant moving the position where the suture fastener is normally held out beyond a nominal position where the hammer and anvil could act properly on it when crimping. However, in embodiments such as the one illustrated in FIG. 2A, the expanded receiving face 56 also has a collar recess 60, configured to hold a collar 62 of the suture fastener 54. With a collar recess 60, an expanded receiving face 56 can be implemented while a desired position of the suture fastener 54 can be maintained relative to the hammer 48 and the anvil 50.

These are advantages which have been identified in the inventive concept, but it was still counter-intuitive that expanding the device would be a key to making it smaller. As it turns out, however, and without being limited to one particular theory, expanding the receiving face 56 as described above provides additional structural support to the hammer 48 and anvil 50 pieces which may be coupled directly or indirectly to the expanded receiving face 56. This additional support further enables the reduction of outer hammer 48 and/or anvil 50 material near where the hammer 48 and anvil 50 contact the shaft 46 and away from the surfaces of the hammer 48 and anvil 50 which come together. This allows a smaller diameter shaft 46 to be used while still maintaining the ability to work with an existing size suture fastener 54 and to impart the same crimping profiles into the suture fastener 54. In fact, use of the expanded receiving face 56 design has enabled the successful manufacture and testing of crimping instruments with an outside diameter of approximately 0.177 inches versus the previous outside diameter of approximately 0.203 inches, a 12% reduction in outside diameter while providing the exact same sized crimpable suture fastener. Other embodiments may show even greater size reductions, and all of these reductions may enable even smaller devices in remote, constrained surgical areas, thereby helping to improve patient outcomes.

Figure 3:
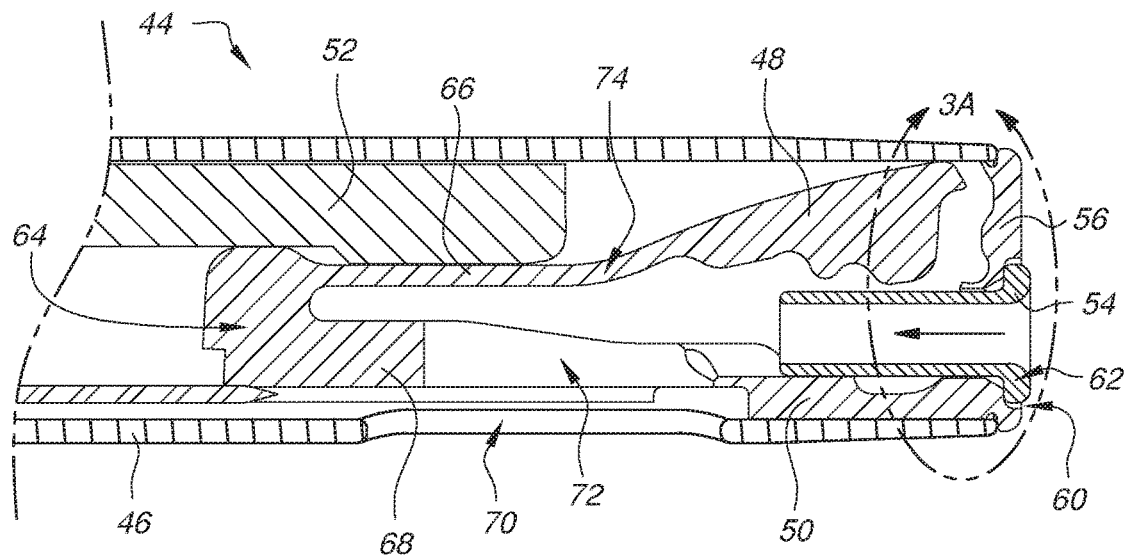
FIG. 3 illustrates, in cross-sectional view, the distal end of the instrument for crimping a suture fastener from FIG. 2 with a crimpable sleeve installed in one embodiment of an expanded receiving face.

FIG. 3 shows the distal end 44 of the instrument from FIG. 2 with a crimpable suture fastener 54 (crimpable sleeve) installed in the collar recess 60 of the expanded receiving face 56. In this embodiment, the hammer 48 and the anvil 50 are part of a crimping member 64 which has first and second opposed legs 66, 68. The hammer 48 is located near the end of the first opposed leg 66, while the anvil 50 is located near the end of the second opposed leg 68. The shaft 46 and the second leg 68 define respective openings 70, 72 to allow suture ends (not shown here, but will be shown later) to pass from the collar 62, through and out of the other end of the suture fastener 54, between the first and second opposing legs 66, 68, and then out through openings 70, 72 to an area outside of the shaft 46. In this embodiment, part of the suture fastener 54 rests against the anvil 50, while the hammer 48 is positioned just above the suture fastener 54. In other embodiments, the hammer 48 may be configured to be just touching or biased against the suture fastener 54 to help hold it in place before crimping. Depending on the embodiment, this starting position of the hammer 48 can be influenced by the configuration of a flexure portion 74 in the first opposing leg 66. Different flexure 74 options will be discussed later in this specification.

Figures 3A, 3B, 3C:
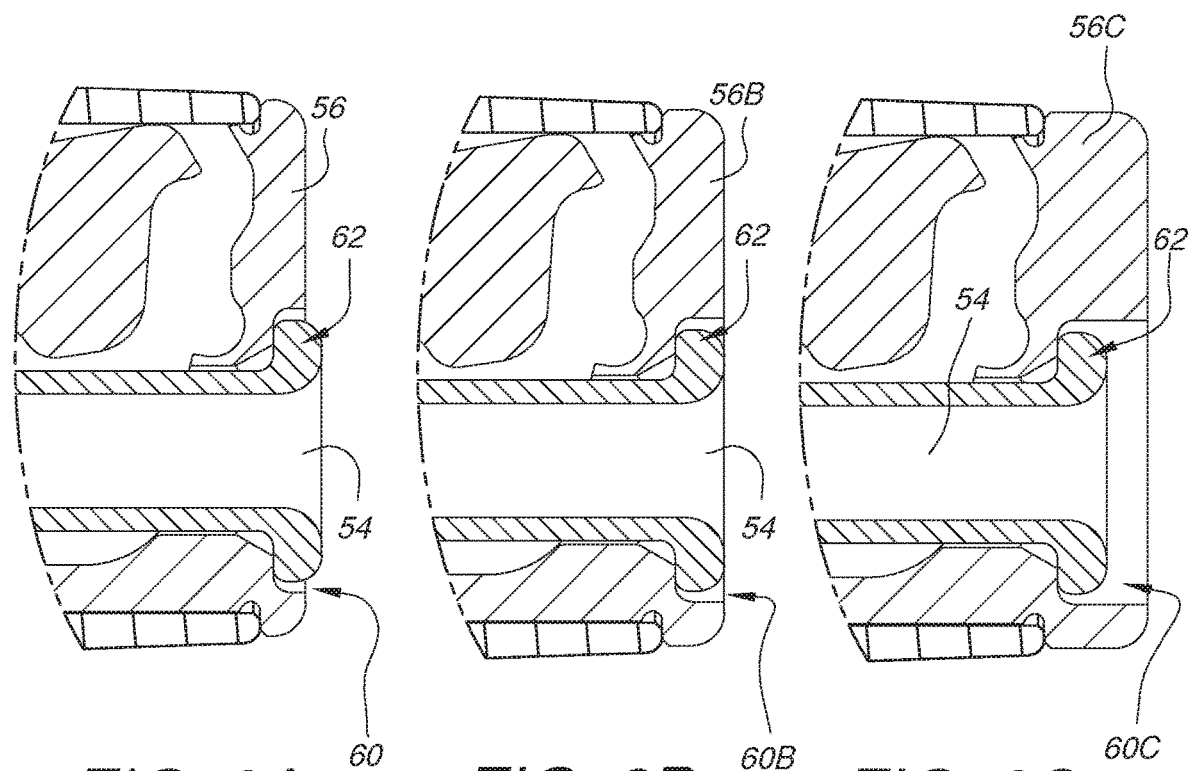
FIG. 3A shows an enlarged cross-sectional view of the expanded receiving face from the instrument embodiment shown in FIG. 3.
FIGS. 3B-3C are enlarged cross-sectional views of other embodiments of an expanded receiving face for an instrument for crimping a suture fastener.

FIG. 3A shows an enlarged cross-sectional view of the expanded receiving face 56 from the instrument embodiment shown in FIG. 3. For some embodiments, such as the one shown in FIG. 3A, the collar recess 60 is a partial recess in the sense that, despite the collar recess 60, a portion of the suture fastener's collar 62 still sticks out past the end of the expanded receiving face 56. In other embodiments, such as the one illustrated in FIG. 3B, the collar recess 60B is a flush recess because the suture fastener's collar 62 is flush with the end of the alternate expanded receiving face 56B. In still other embodiments, such as the one illustrated in FIG. 3C, the collar recess 60C is an over-deep recess because the suture fastener's collar 62 is set below the end of the alternate expanded receiving face 56C.

Figure 4:
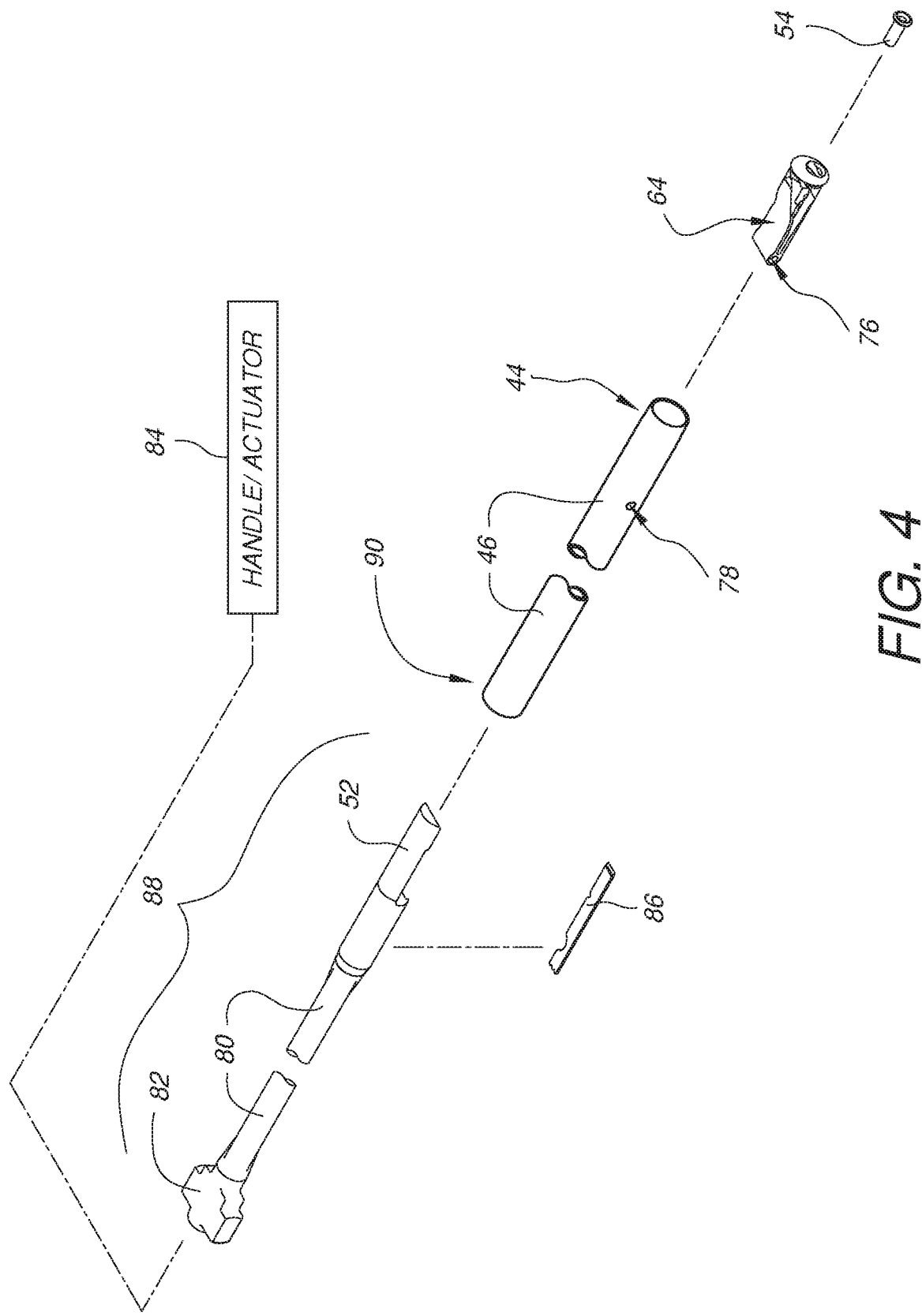
FIG. 4 is a partially schematic, exploded perspective view of one embodiment of an instrument for crimping a suture fastener.

Before discussing the operation of the instrument for crimping a suture fastener in more detail, it is helpful to understand how the parts of this device embodiment are assembled together. Accordingly, FIG. 4 is a partially schematic, exploded perspective view of one embodiment of an instrument for crimping a suture fastener. The crimping member 64, discussed previously, can be inserted into the distal end 44 of the shaft 46. A recess 76 in the crimping member 64 can be pinned, staked, or otherwise held in place at a corresponding pinning location 78 in the shaft 46 in order to keep the crimping member 64 from coming out of the shaft 46. The pusher 52 can be coupled to or an extension of a push rod 80. The push rod 80 may include a coupling feature 82 configured to be coupled to a handle/actuator 84.

The actuator 84 can be any type of manually operated or automated device, such as, but not limited to a lever, an arm, a knob, a slide, a motor, a solenoid, or any plurality and/or combination thereof which can be used to slide the pusher 52 back and forth within the shaft 46 along a path which is substantially parallel to a longitudinal axis of the shaft 46. One suitable actuator 84 is the handle and lever disclosed in U.S. Pat. No. 7,235,086 entitled "CRIMPING INSTRUMENT WITH MOTION LIMITING FEATURE", the entirety of which is hereby incorporated by reference.

A suture cutting blade 86 can be coupled to and/or held by the pusher 52. Operation of the cutting blade 86 will be discussed in more detail later in this specification. In other embodiments, the cutting blade 86 may be a continuous extension of the pusher assembly 88, rather than a separate part from the pusher 52. The pusher assembly 88 can be placed into the proximal end 90 of the shaft 46 and into engagement with the crimping member 64. As will be described later, the crimping member 64 may include one or more blade steering guides (not easily visible in this view) configured to restrict lateral movement of the suture cutting blade 86 away from the direction substantially parallel to the longitudinal axis of the shaft 46.

Figure 5:
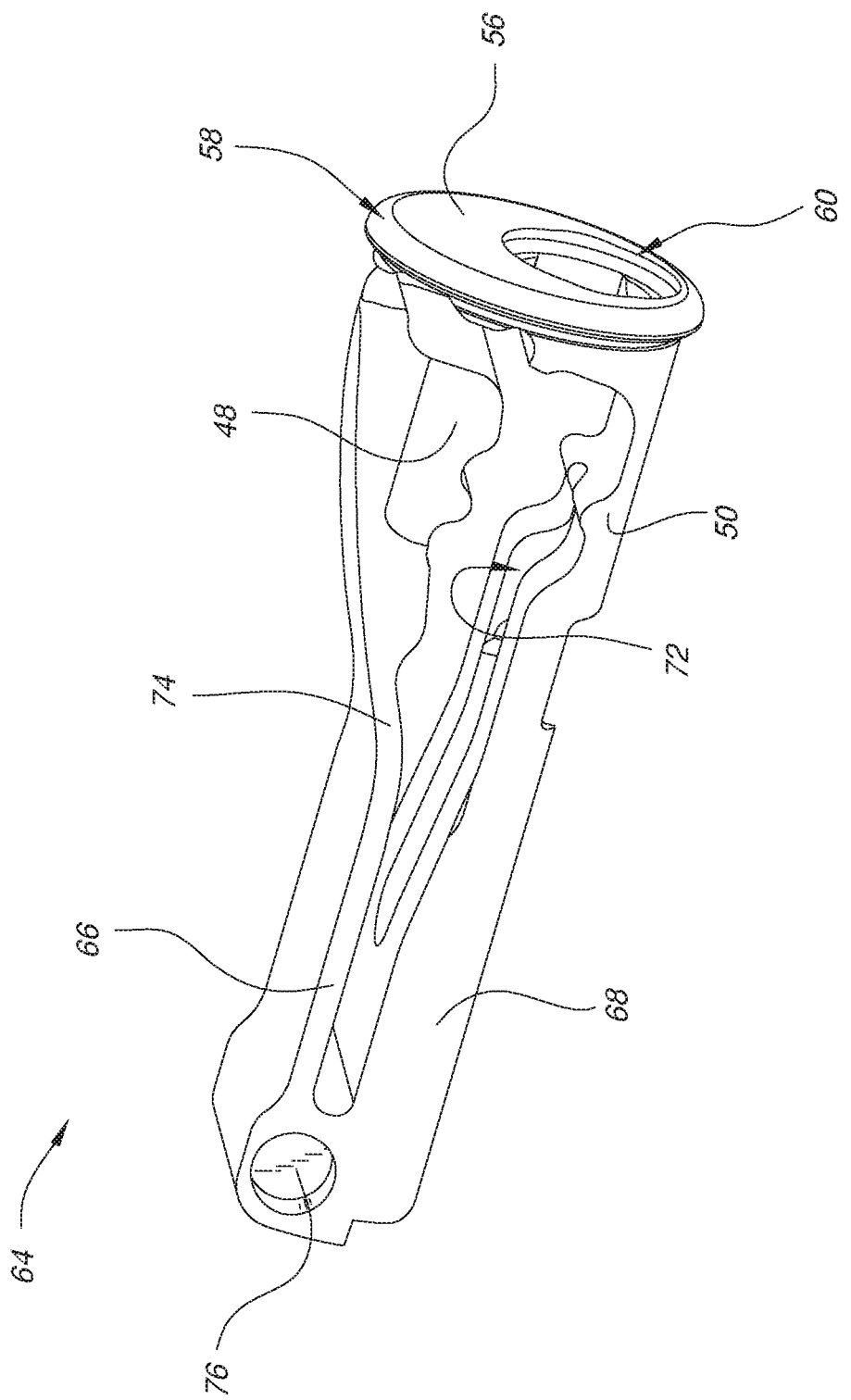
FIG. 5 is a perspective view of one embodiment of a crimping member having a hammer, an anvil, and an expanded receiving face.

FIG. 5 is a perspective view of one embodiment of a crimping member 64 having a hammer 48, an anvil 50, and an expanded receiving face 56. The crimping member 64 has first and second opposing legs 66, 68 which are configured to resiliently bias the hammer 48 and anvil 50 apart unless urged together by the pusher (not shown in this view). In this embodiment, the expanded receiving face 56 is an extension of the second opposing leg 68, past where the anvil 50 is located. In other embodiments, the extended receiving face 56 could be an extension of the hammer 48, for example in embodiments where the hammer 48 does not move while the anvil does. In still other embodiments, it is possible for the extended receiving face 56 to be separate from both the hammer 48 and the anvil 50, but it is preferred to have the extended receiving face 56 be an extension of the leg including the anvil 50 as shown in the embodiment of FIG. 5. The collar recess 60, the flexure portion 74, the recess 76, the opening 72 defined by the second leg 68, and the rounded edge 58 of the expanded receiving face 56, all discussed previously, can be seen in more detail the view of this embodiment.

Figure 6:
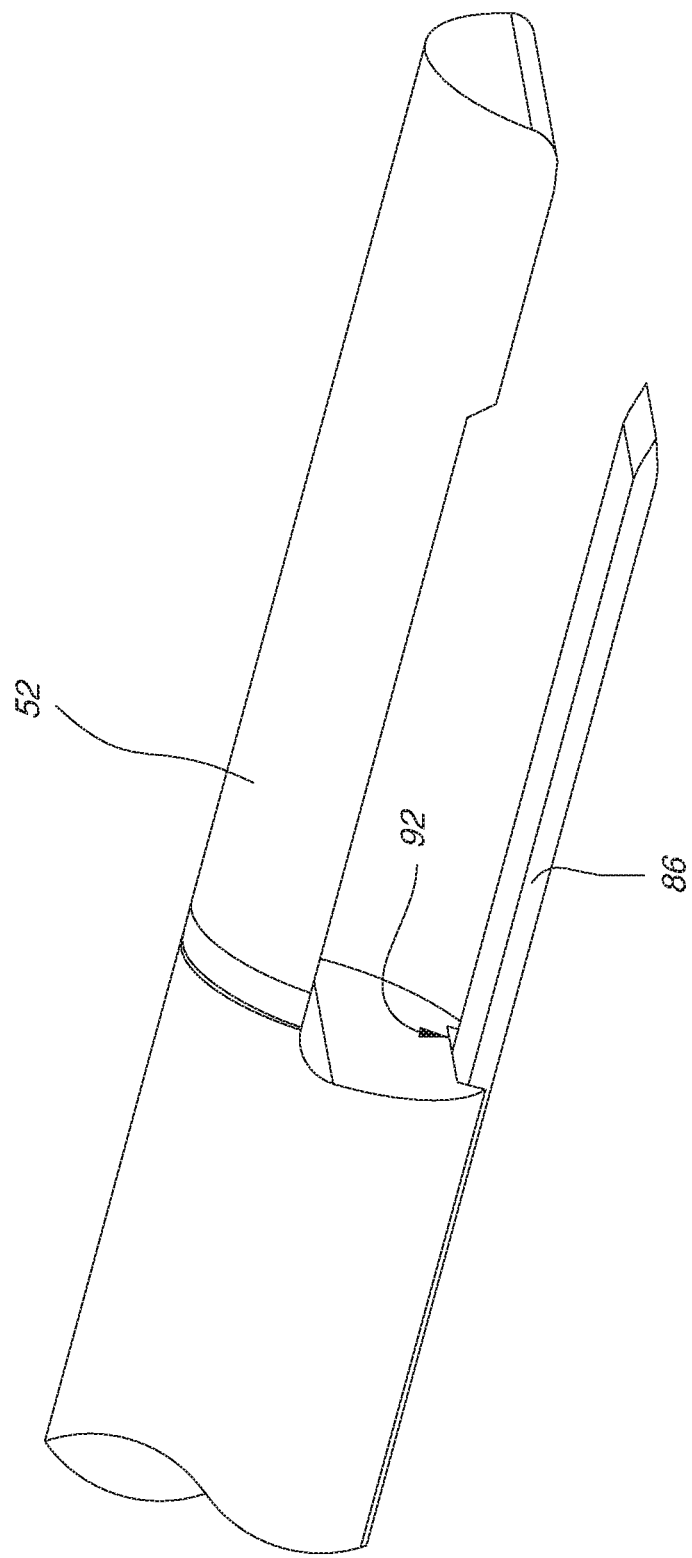
FIG. 6 is a perspective view of one embodiment of a pusher configured to engage a hammer. In this embodiment, a suture cutting blade is coupled to the pusher.

FIG. 6 is a perspective view of one embodiment of a pusher 52 configured to engage a hammer (not shown in this view). In this embodiment, a suture cutting blade 86 is coupled to the pusher 52. The pusher 52 can include a contoured notch 92 to help advance and retract the blade 86. Those skilled in the art will know a variety of ways a blade 86 could be attached to the pusher 52. The blade 86 can be configured to extend forward relative to the end of the pusher 52 so that the suture blade 86 is in a position to cut suture ends after or just as the suture fastener is crimped.

Figure 8:
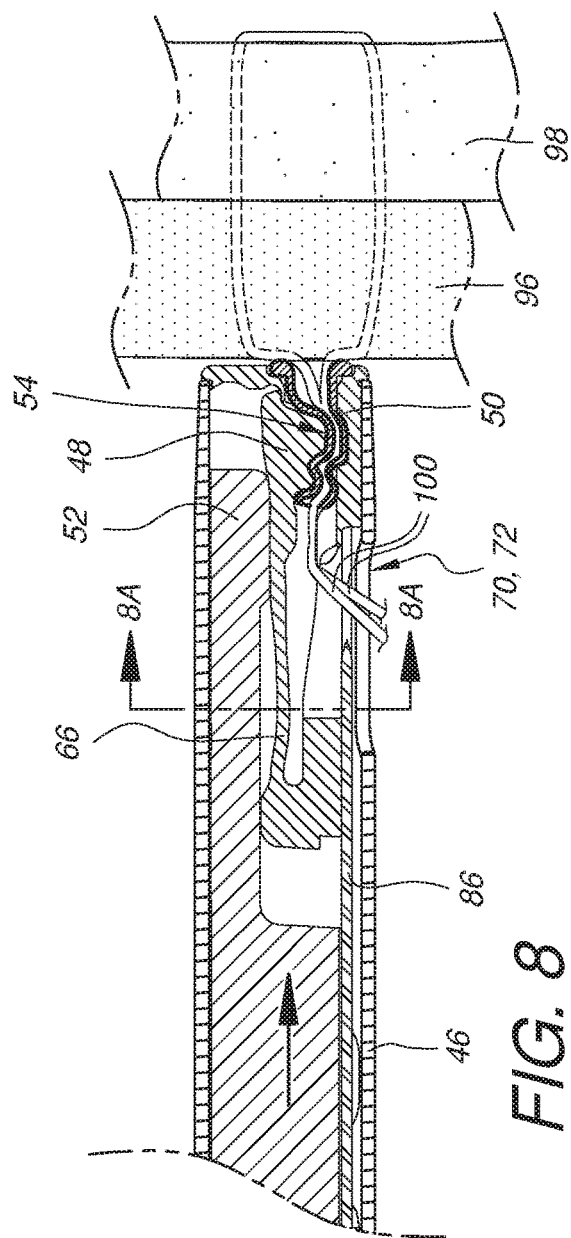
FIG. 8 is a partial cross-sectional side view of the embodied instrument for crimping a suture fastener from FIG. 7 with a pusher advanced to a first position where the hammer is forced down onto the crimpable sleeve, towards the anvil, resulting in a suture holding crimp being formed in the crimpable sleeve.
Figure 8A:
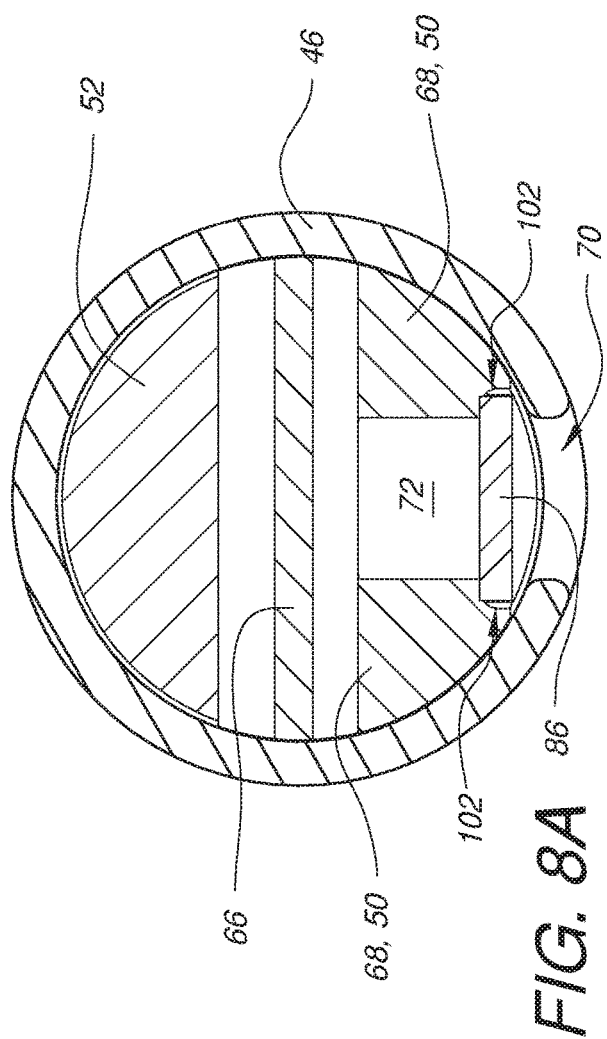
FIG. 8A is a cross-sectional view taken along line 8A-8A from FIG. 8, looking down the device shaft, and illustrating one embodiment of a blade steering guide formed in the anvil of the instrument for crimping a suture fastener.
Figure 9:
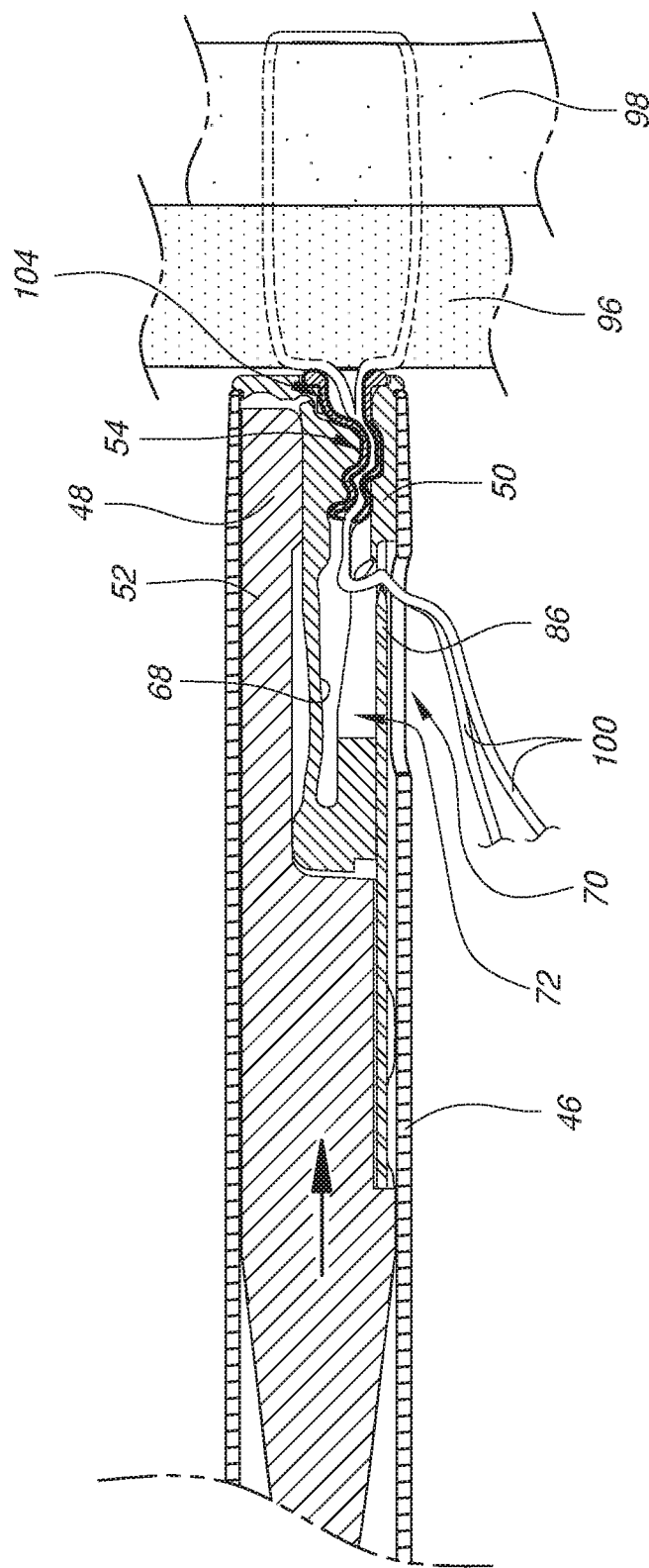
FIG. 9 is a cross-sectional side view of the embodied instrument for crimping a suture fastener from FIG. 8 with the pusher advanced to a second position where a blade coupled to the pusher is cutting the free suture ends protruding from the crimpable sleeve.

FIGS. 7, 8, and 9 illustrate the operation of a surgical instrument embodiment for crimping a suture fastener. FIGS. 7A and 8A illustrate additional detail for this described operation. In particular, FIG. 7 is a partial cross-sectional side view of the embodied instrument for crimping a suture fastener from FIG. 2 (and discussed above). A suture 94 has been secured into one or more objects 96, 98 for example, a tissue prosthetic valve sewing ring and underlying aortic annular tissue. The suture ends 100 have been passed through a suture fastener 54 (crimpable sleeve) loaded into the expanded receiving face 56 on the distal end 44 of the instrument. The suture ends 94 also pass through the openings 72, 70, defined by the second opposed leg 68 and the shaft 46, respectively, and accordingly exit the bottom of the instrument. This loading of the suture 94 can be accomplished, for example, with a snare device, not shown, but known to those skilled in the art. FIG. 7A is a non-cross-sectioned bottom view of the device and situation shown in FIG. 7.

The pusher 52 is resting on a portion of the first opposed leg 66 which does not substantially force the hammer 48 into contact with the suture fastener 54. In other embodiments, the first opposed leg may include a pre-load bump (not shown in this embodiment, but examples will be shown later) which would cause the hammer to be pre-loaded lightly against the suture fastener 54 in order to help hold it in place prior to crimping. The suture cutting blade 86 is positioned adjacent to the openings 70, 72, but cannot cut the suture ends 100 at this point.

As shown in the partial cross-sectional side view of FIG. 8, the pusher 52 has been advanced by an actuator (not shown) to a first position where the hammer 48 is forced down onto the suture fastener 54, towards the anvil 50, resulting in a suture holding crimp being formed in the suture fastener 54. Before the pusher 52 is advanced to the position shown in FIG. 8, the expanded receiving face 56 can be moved into contact with at least one of the one or more sutured objects 96, 98 as tension is applied to the suture ends 100 to remove suture slack prior to crimping. When the pusher 52 has been advanced to the first position shown in FIG. 8, the suture cutting blade 86 is also starting to cross the openings 70, 72, but the suture ends 100 are not in a position to be cut yet.

FIG. 8A is a cross-sectional view taken along line 8A-8A from FIG. 8, looking down the device shaft 46, and illustrating one embodiment of blade steering guides 102 formed in the anvil 50. Since the anvil 50 is coupled to or an extension of the second opposed leg 68, the blade steering guides 102 could also be said to be formed in the second leg 68 as well. The one or more blade steering guides 102 are configured to help restrict lateral movement of the suture cutting blade 86 away from a direction substantially parallel to the longitudinal axis of the shaft 46.

FIG. 9 is a cross-sectional side view of the embodied instrument for crimping a suture fastener from FIG. 8 with the pusher 52 advanced to a second position where the blade 86 coupled to the pusher 52 has advanced to the point where it is able to cut the suture ends 100. Depending on the configuration, the blade 86 can extend towards the distal end of the device far enough to cut the suture ends 100 without any assistance from a user of the device. In other embodiments, the blade 86 can extend to the point where the suture ends 100 are pinched against the blade 86, and the user controls the moment when the suture cut is completed by pulling on the suture ends 100. When the pusher 52 is in this second position, the hammer 48 does not have to crimp the suture fastener 54 further due to opposing surfaces 104 on the hammer 54 and anvil 50 which can be arranged to limit the hammer 48 motion.

As mentioned previously (for example, with regard to FIG. 5), some embodiments of an instrument for crimping a suture fastener to a surgical suture can include a crimping member having first and second opposed legs 66, 68. In such embodiments, the hammer 48 may be located near the end of the first opposed leg 66, while the anvil 50 may be located at the end of the second opposed leg. The first opposed leg 66 may also include a flexure portion. The flexure flexes to allow the hammer 48 to be moved towards the anvil 50 by the pusher 52. FIGS. 10A-10J illustrate different crimping members having a variety of flexure embodiments. For example, the embodiments of FIGS. 10A and 10B have a straight flexure 106 which is oriented to be substantially perpendicular to the expanded receiving face 56 when not being flexed under a load. The embodiment of FIG. 10B also has a pre-load bump 108 on the flexure 106. The pre-load bump 108 can be used in some embodiments to provide a slight interference with the pusher (not shown here) before the pusher is advanced into contact with the hammer 48. This slight interference can deflect the hammer 48 slightly against a suture fastener (not shown) held in the expanded receiving face 56 in order to keep the fastener from falling out of the device prior to crimping.

Figure 10A:
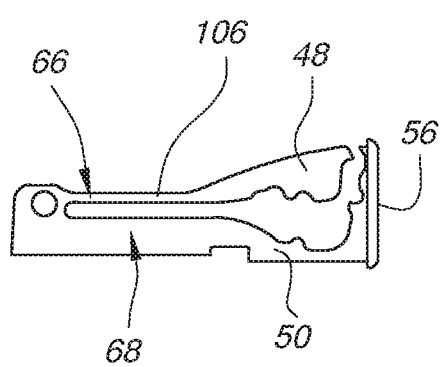
FIGS. 10A-10J illustrate different crimping members having a variety of flexure embodiments.
Figure 10B:
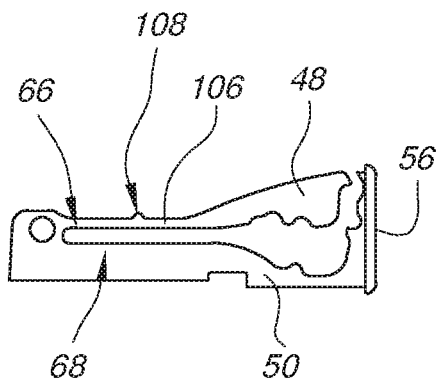
Figure 10C:
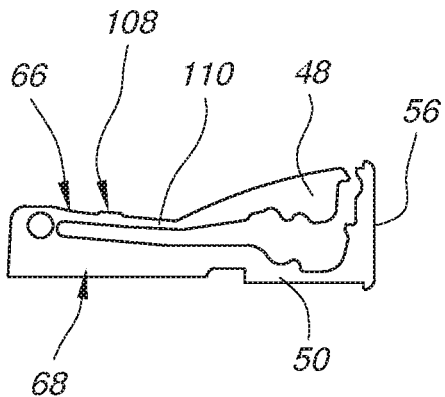
Figure 10D:
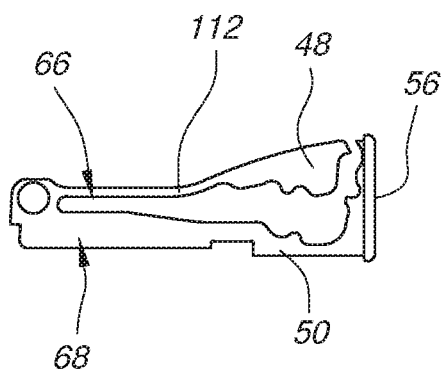
Figure 10E:
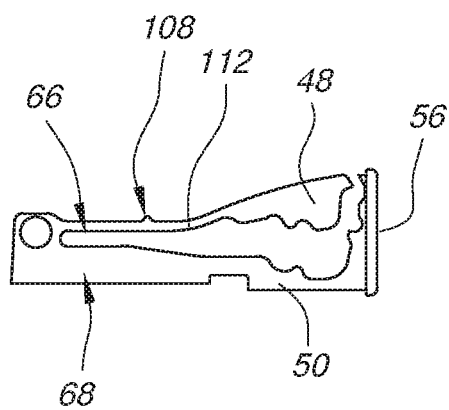
Figure 10F:
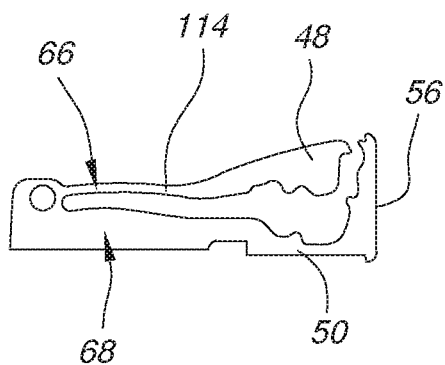
Figure 10G:
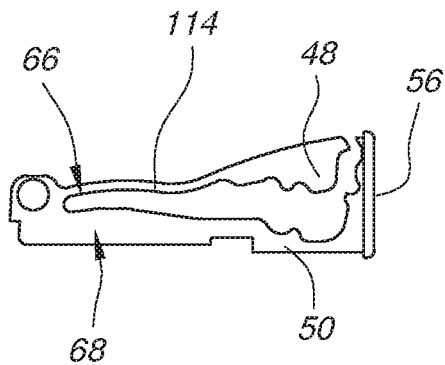
Figure 10H:
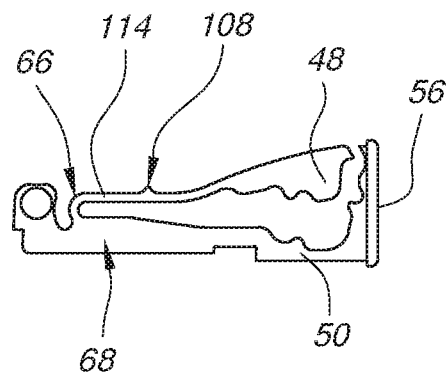
Figure 10I:
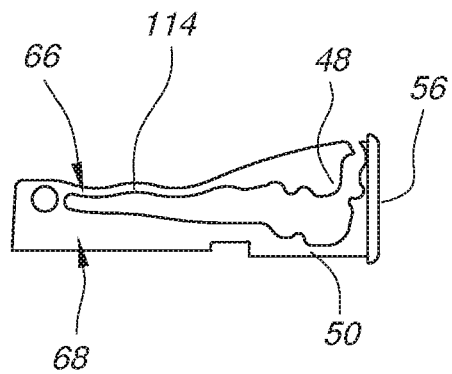
Figure 10J:
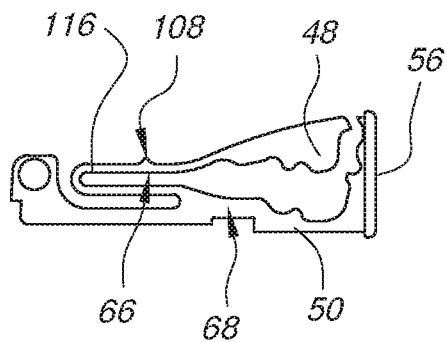

FIG. 10C illustrates another embodiment of a crimping member having a straight flexure 110, however this straight flexure is not substantially perpendicular to the expanded receiving face 56 when not being flexed under a load. The embodiment of FIG. 10C also includes a pre-load bump 108, the features of which have been discussed above.

Some flexure embodiments will not be straight. As examples, the crimping member embodiments of FIGS. 10D and 10E include an arced flexure 112 having a single bend in the flexure 112. The embodiment of FIG. 10E also includes a pre-load bump 108, the features of which have been discussed above. Other crimping member embodiments may have wavy flexures with more than a single bend. For example, the crimping member embodiments of FIGS. 10F-10I include a wavy flexure 114. The embodiment of FIG. 10H also includes a pre-load bump 108, the features of which have been discussed above. Other flexure embodiments are possible, including, but not limited to a hairpin flexure that doubles back on itself. For example, the crimping member embodiment of FIG. 10J includes a hairpin flexure 116. The embodiment of FIG. 10J also includes a pre-load bump 108, the features of which have been discussed above.

Figure 11:
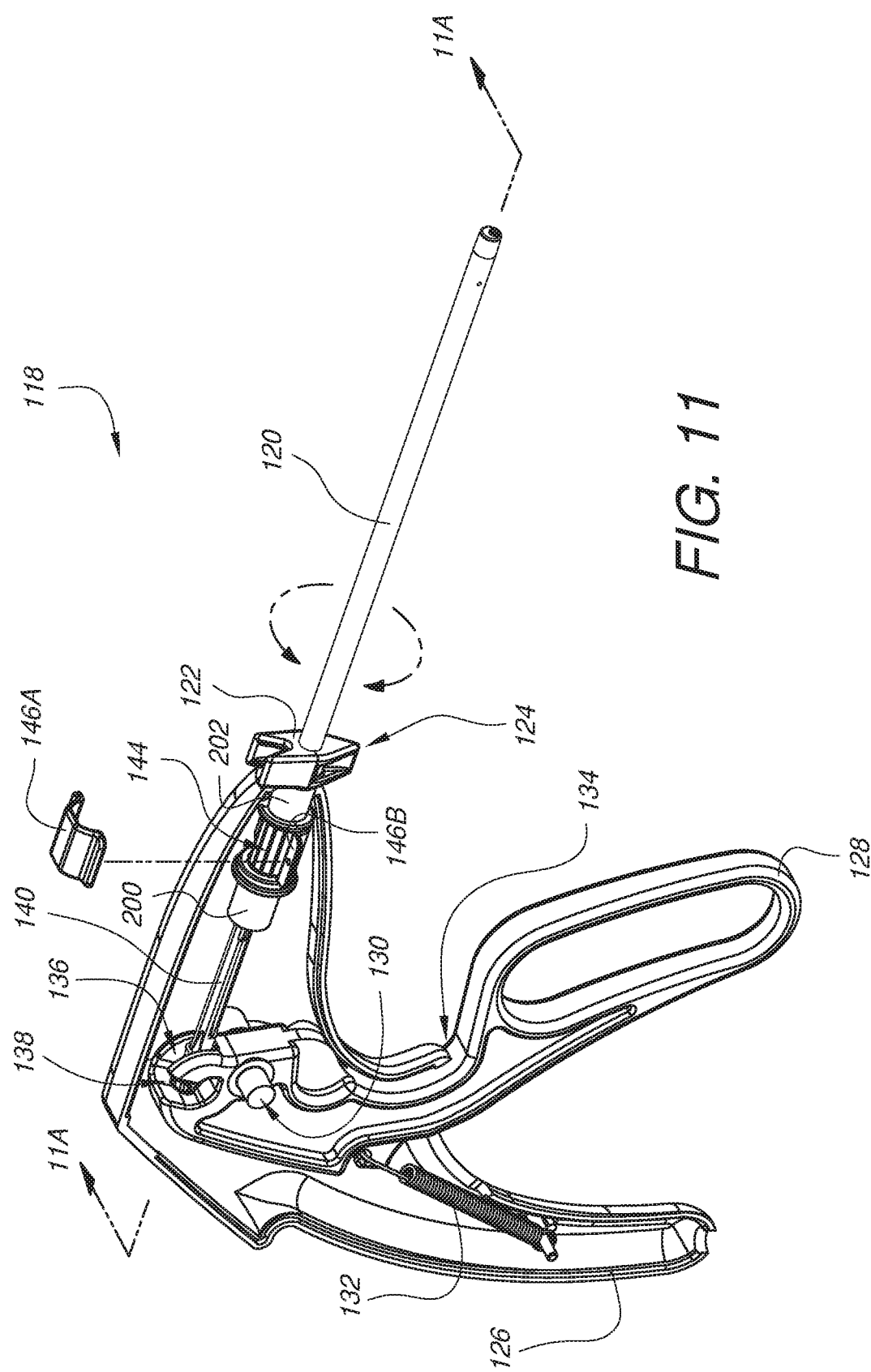
FIG. 11 is a partially exposed perspective view of one embodiment of an instrument having a rotatable shaft for crimping a suture fastener.

The embodiments of a crimping instrument with reduced dimension and compatibility with an existing, proven knot, which have been discussed above, also have tissue protection features, such as the sharp edge avoidance made possible by the expanded receiving face on smaller dimensioned devices. Other embodiments may include an additional tissue protection feature, for example a rotatable shaft which enables an operator to orient the direction of the crimped suture fastener to orient the direction of the suture tails away from delicate structures. As one example, FIG. 11 is a partially exposed perspective view of one embodiment of an instrument 118 for crimping a suture fastener. The instrument 118 has a rotatable shaft 120 with a rotation knob 122 coupled to the shaft 120 and configured to simultaneously rotate the shaft 120 and the push rod 140. The rotation knob 122 can have a variety of shapes, and in some embodiments, the rotation knob 122 could be the shaft itself. In this embodiment, the rotation knob 122 also includes a crimp direction indicator 124 that correlates with a direction that the crimps formed in a suture fastener will direct trimmed suture tails. Depending on the embodiment, the crimp direction indicator 124 could point in a direction the suture tails will point. In other embodiments, the crimp direction indicator 124 could point in the opposite direction. In either case, or with any readily predictable correlation between the crimp direction indicator 124 and the crimped fastener produced by the instrument 118, the operator of the instrument 118 can readily orient the device handle 126 and/or shaft rotation knob 122 to have the suture tails face a desired direction. This tissue protection feature can be especially helpful when installing artificial heart valves, as it may be desirable to have the crimped fasteners direct the suture tails away from the valve so as not to have tissue or valve material contacting the crimped fastener surface or the suture tails. Since it may not always be possible or ergonomically practical for a surgeon to rotate the handle 126 of the device, embodiments having a rotatable shaft 120 offer more orientation flexibility to the surgeon, thereby enabling tissue and prosthetic protection.

Figure 11A:
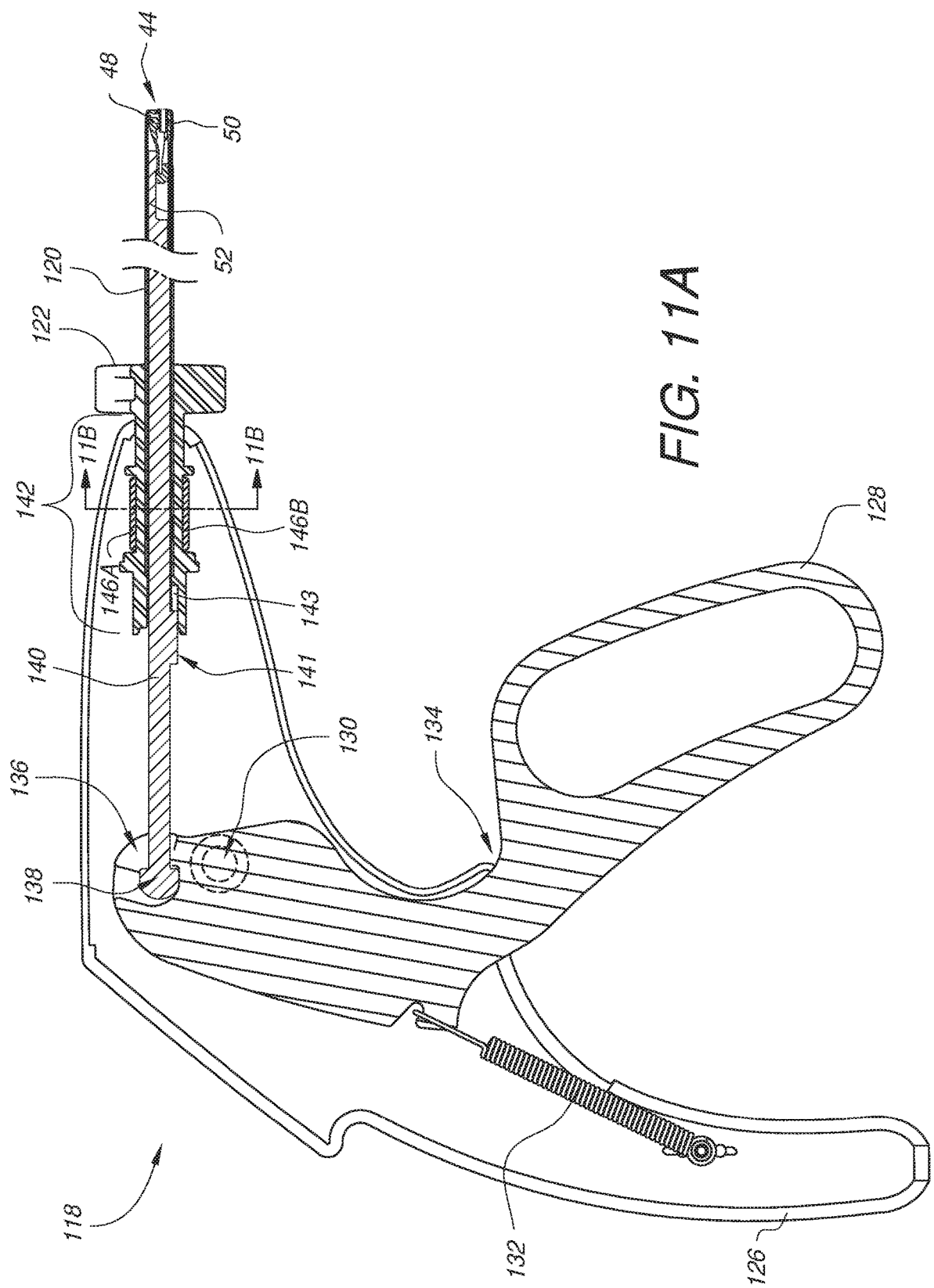
FIG. 11A is a side cross-sectional view of the instrument for crimping a suture fastener from FIG. 11.

An actuator lever 128 is pivotably coupled to the handle 126 at pivot point 130. A biasing spring 132 is coupled between the handle 126 and the actuator 128, rotating the actuator 128 counterclockwise around the pivot point 130 until the actuator 128 contacts the handle 126 at stop point 134. The actuator 128 also has a socket 136 which receives a ball end 138 of push rod 140. FIG. 11A is a side cross-sectional view of the instrument 118 from FIG. 11. Push rod 140 may be coupled to the pusher 52 or continuous with the pusher 52 as shown in FIG. 11A. When the actuator 128 is in the resting position shown, the push rod 140 is retracted away from the distal end 44 of the shaft 120. In this position, as discussed above, the pusher 52 is not engaging the hammer 48. However, if the actuator 128 is squeezed towards the handle 126, the actuator socket 136 will advance the push rod 140 (and therefore the pusher 52) towards the distal end 44, thereby enabling the pusher 52 to engage the hammer 48 as discussed above in order to crimp a suture fastener.

Figure 11B:
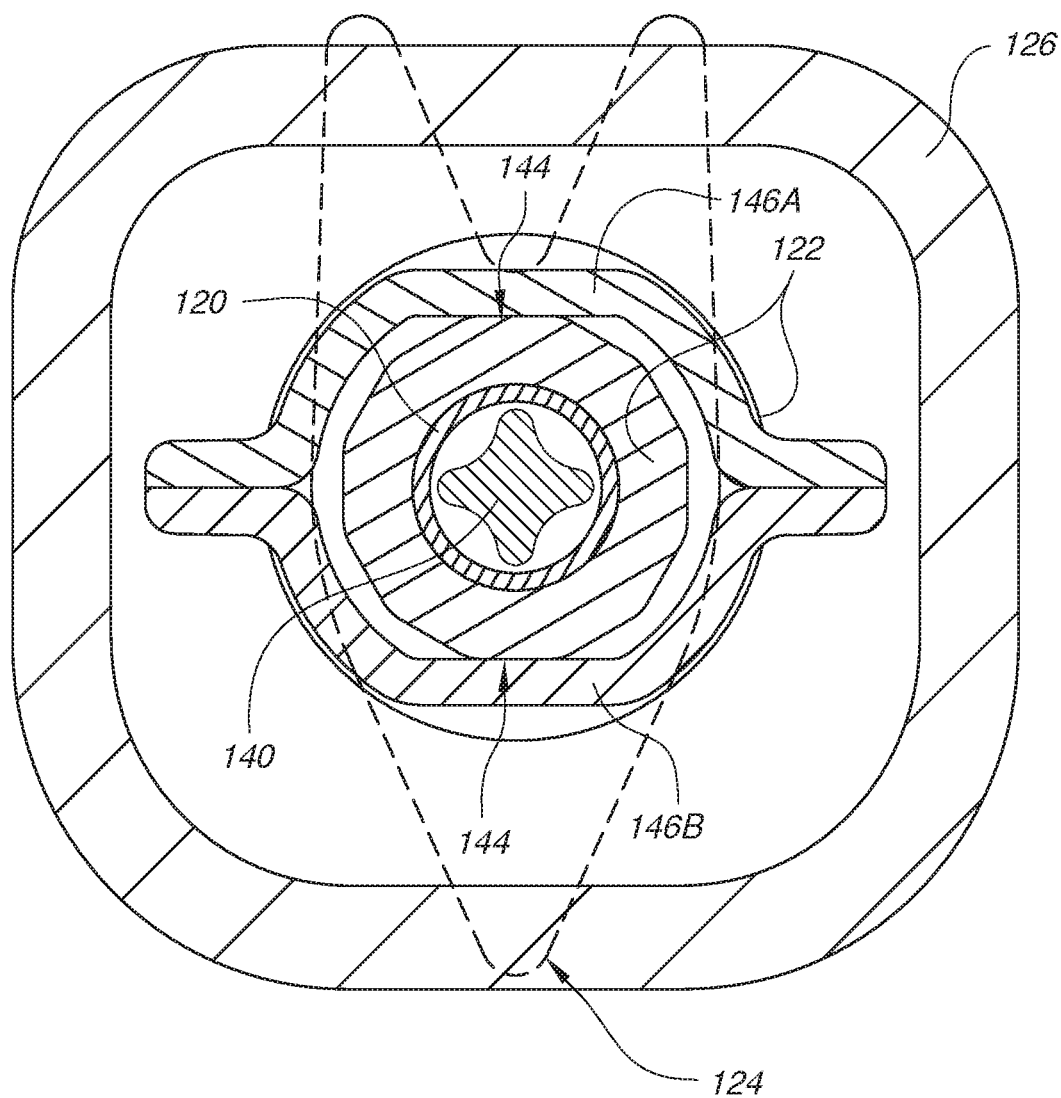
FIG. 11B is a cross-sectional view of the instrument for crimping a suture fastener from FIG. 11A taken along line 11B-11B.

The rotation knob 122 has a portion 142 which extends into the handle 126. The handle 126 can include structure to rotatably support this portion 142 of the rotation knob 122. For clarity and visualization of other structures, rotational supports are not shown, but those skilled in the art will clearly know that such supports may easily be incorporated. A portion of the rotation knob 122 may include one or more facets 144 which can be sized to engage a constraint, here illustrated as an embodiment with an upper constraint 146A and a lower constraint 146B. Those skilled in the art will recognize that facets may include but are not limited to, such structures as recesses, bumps, and angled edges. For convenience, however, such structures and their equivalents will simply be referred to herein as facets. A profile of the facets 144 and the constraints 146A, 146B can be seen in the view of FIG. 11B, which is a cross-sectional view taken along line 11B-11B from FIG. 11A, looking from a location in the handle towards the distal end of the device. When a facet 144 is flat against the constraint 146A, 146B, rotation of the shaft 120 (to which the rotation knob 122 is coupled) will be resisted. However, the facets 144 (of the rotation knob 122) and/or the constraints 146A, 146B may be made from a flexible material so that an external force applied to the rotation knob 122 can cause the facets 144 and/or the constraint 146A, 146B to deflect or deform, allowing the shaft 120 to rotate until other facets 144 contact the constraints 146A, 146B. The mating of the facets 144 with the constraint 146A, 146B can be felt by the user, thereby enabling indexing of the shaft rotation positions. In the embodiment illustrated in FIG. 11B, the rotation knob 122 has twelve facets, however other embodiments may have a different number and/or type of facets. Other embodiments may not include facets, but may be configured to include rotational resistance so that the shaft does not rotate at undesired times.

The rotation knob 122 is coupled to the shaft 120. The push rod 140 is configured to be able to slide through the rotation knob 122 in directions parallel to the longitudinal axis of the shaft 120. In this embodiment, the push rod 140 also has one or more keyed features 141 which can slide longitudinally in a mating fashion within corresponding one or more slots 143 in the rotation knob 122. The one or more keyed features 141 permit longitudinal movement of the push rod 140 for crimping operations. When the rotation knob 122 is rotated, however, the one or more keyed features 141 engaged the corresponding one or more slots 143 to rotationally couple the push rod 140 to the rotation knob 122. In this way, since the rotation knob 122 is also coupled to the shaft 120, both the push rod 140 and the shaft 120 are rotated directly by the rotation knob 122. In other embodiments, the rotation knob 122 may only be rotationally coupled to the shaft 120. In such embodiments, when the knob 122 is rotated, the rotational force would have to be transferred to the push rod 140 via the crimping member and hammer in the distal end of the shaft 120. While such an embodiment is possible, it is not ideal because of the larger stresses placed on the components in the distal end of the device.

Figure 12A:
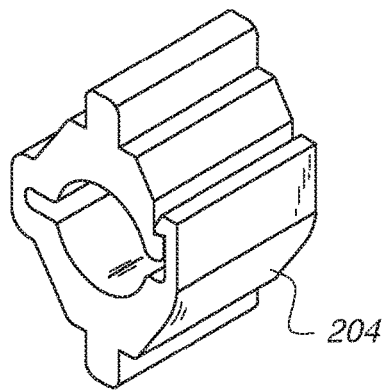
FIGS. 12A and 12B illustrate one embodiment of a proximal bushing in both closed and open configurations, respectively.
Figure 12B:
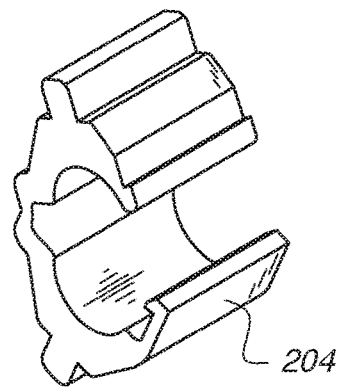

The instrument 118 of FIG. 11 includes a rotation adapter (to be discussed in more detail below) having a proximal journal 200 and a distal journal 202. While the handle 126 may include bushing surfaces (not shown) within which the journals 200, 202 can spin, this has been shown to be a difficult proposition when the handle 126 material (of which the bushings are made) and the journal 200, 202 material are the same. The potential difficulty can arise because the handle 126 may be ultrasonically welded together, and the welding process can cause the journals 200, 202 to become stuck to the bushings made from the handle. As such, it has been discovered that bushings made from a different material than that of the journal surfaces is advantageous. FIGS. 12A and 12B illustrate one embodiment of a proximal bushing 204 in both closed and open configurations, respectively. In the embodiment of FIGS. 12A and 12B, the proximal bushing 204 is a clinch bushing, but other embodiments can be a wide variety of bushing types, including, but not limited to a solid bushing, a split bushing, and a flange bushing.

Figure 13:
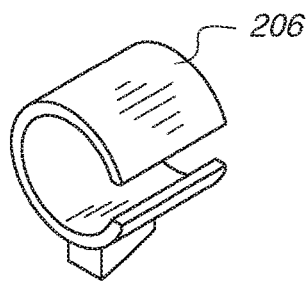
FIG. 13 illustrates one embodiment of a distal bushing.

Likewise, FIG. 13 illustrates one embodiment of a distal bushing 206. In the embodiment of FIG. 13, the distal bushing 206 is a split bushing, but other embodiments can be a wide variety of bushing types, including, but not limited to a clinch bushing, a solid bushing, and a flange bushing.

Figure 14A:
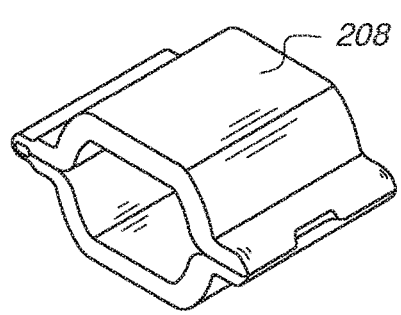
FIGS. 14A and 14B illustrate one embodiment of a rotation constraint in both closed and open configurations, respectively.
Figure 14B:
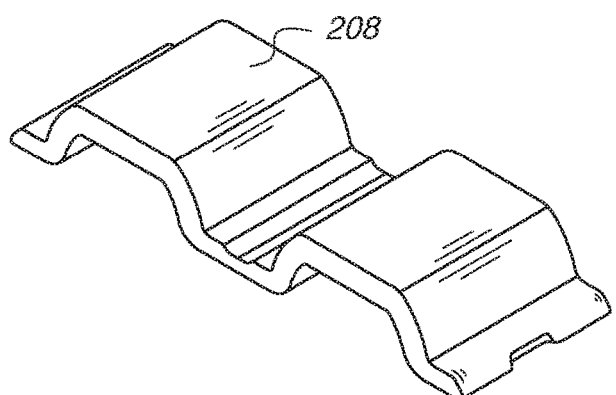

FIGS. 14A and 14B illustrate another embodiment of a rotation constraint 208 in both a closed and open view, respectively. Unlike the multi-piece rotation constraint 146A, 146B from FIG. 11, this constraint 208 is a one-piece clamshell type design.

Figure 15:
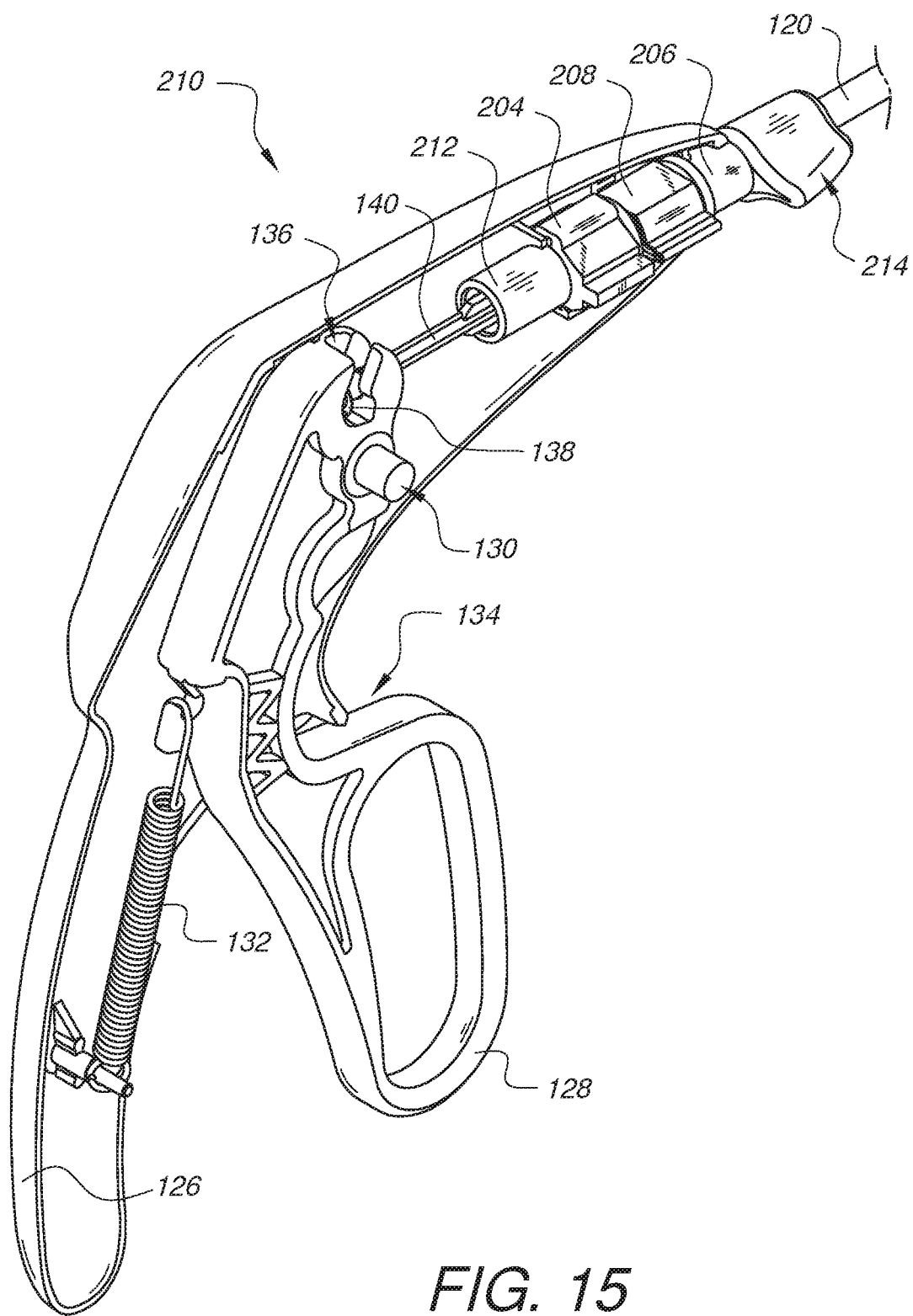
FIG. 15 is a partially exposed perspective view of one embodiment of a minimally invasive surgical device having a rotation adapter supported by the proximal bushing of FIG. 12A and the distal bushing of FIG. 13.

FIG. 15 illustrates a minimally invasive surgical device 210, similar to the instrument 118 of FIG. 11, but with a rotation adapter 212 having a slightly different effector direction indicator 214 (as opposed to the rotation knob 122 of FIG. 11), with a proximal bushing 204 and a distal bushing 206 supporting corresponding journals on the rotation adapter 212, and with rotation constraint 208 limiting free rotation in the absence of a sufficient outside rotational force applied to the effector direction indicator 214. The bushings 204, 206 and the rotation constraint 208 prevent the rotation adapter 212 from coming into contact with the handle 126. Therefore, the handle 126 and the rotation adapter 212 may be made from the same material if desired, for example, ABS plastic, although other embodiments may utilize other materials. The rotation constraint 208 and the bushings 204, 206 may be made from a different material such as PBT, although other embodiments may utilize different materials.

Figure 16A:
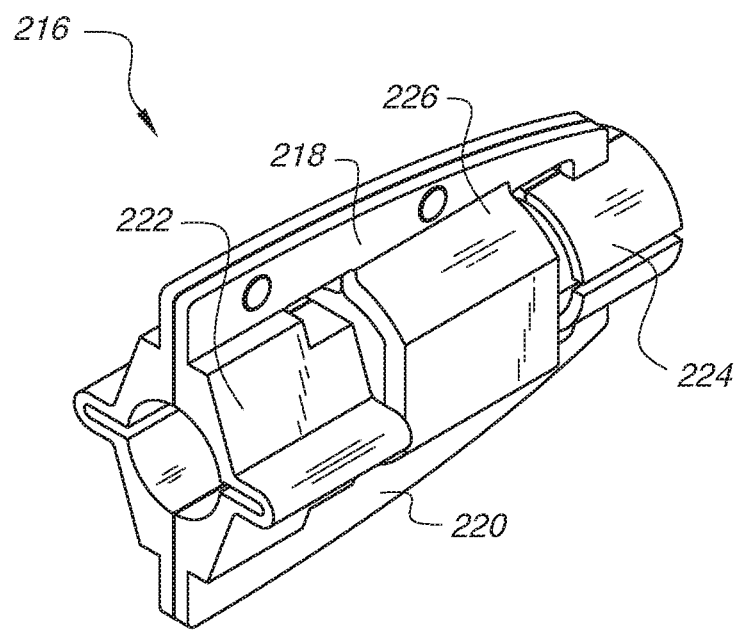
FIGS. 16A and 16B illustrate one embodiment of a rotation adapter receiver in assembled and disassembled forms, respectively.

While the embodiment of FIG. 15 utilizes a separate proximal bushing 204, distal bushing 206, and rotation constraint 208, it has been discovered that it is advantageous to have a rotation adapter receiver which integrates bushings with a rotation constraint in a manner which relieves stress from the rotation constraint. For example, FIG. 16A illustrates one embodiment of an assembled rotation adapter receiver 216. The rotation adapter receiver 216 has opposing beams 218, 220. A proximal bushing 222 is coupled between the opposing beams 218, 220. A distal bushing 224 is also coupled between the opposing beams 218, 220. In this embodiment, the proximal bushing 222 is a clinch bushing, while the distal bushing 224 is a split bushing. The rotation adapter receiver 216 also has a rotation constraint 226 coupled between the opposing beams 218, 220 and positioned between the proximal and distal bushings 222, 224. In this embodiment, the rotation adapter receiver 216 of FIG. 16A is constructed from two identical parts. In other embodiments, the components which make up a rotation adapter receiver need not be identical, however, if the parts are identical, then the manufacturing process is simplified.

Figure 16B:
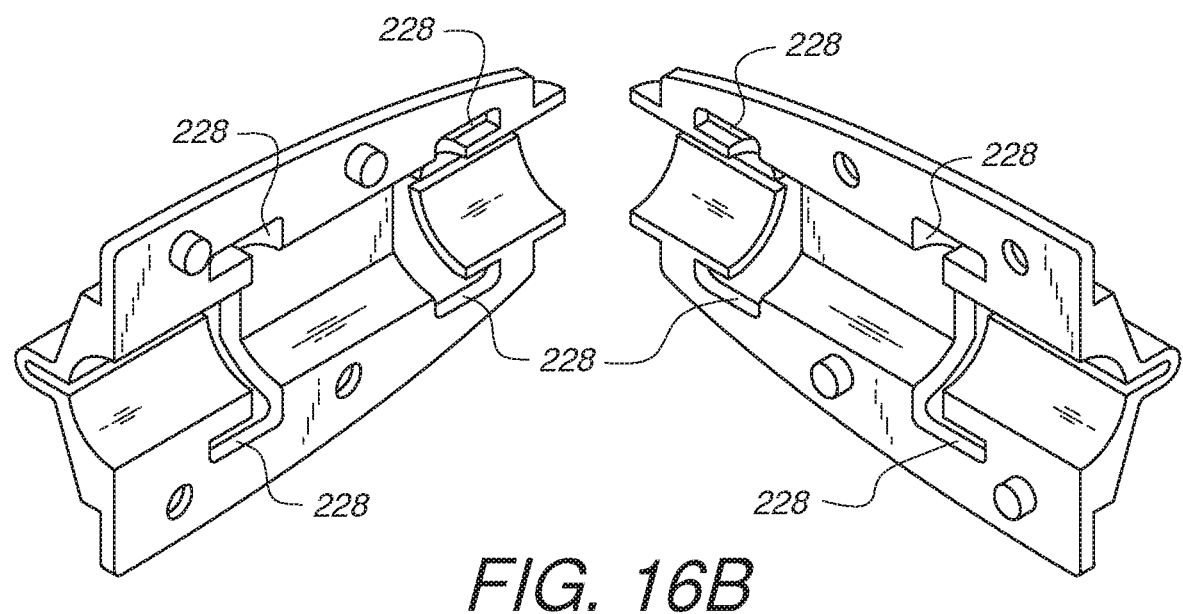
Figure 17:
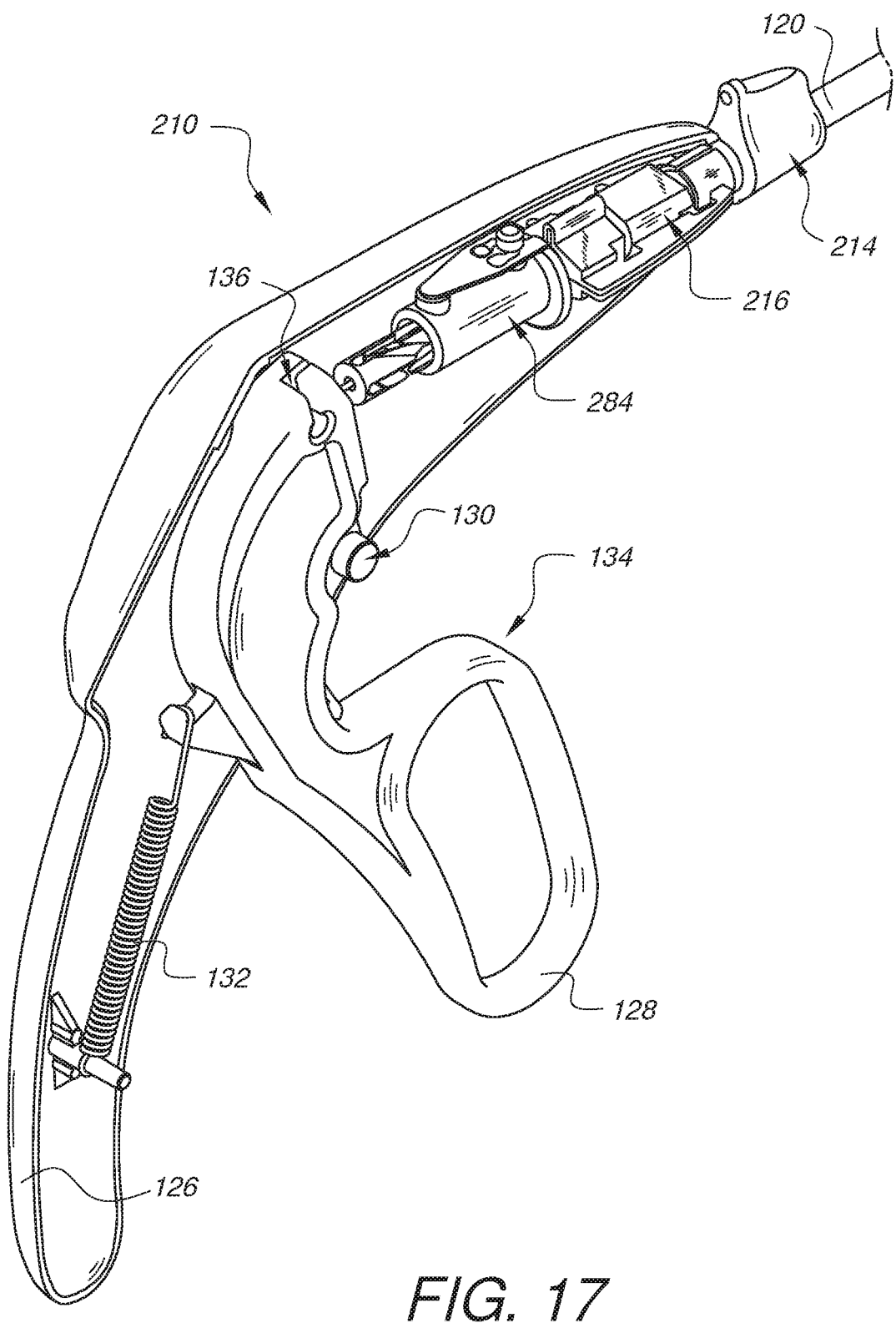
FIG. 17 is a partially exposed perspective view of one embodiment of a minimally invasive surgical suturing device having a rotation adapter supported by the rotation adapter receiver of FIG. 16A.

The identical parts which make up the rotation adapter receiver 216 are shown separated in FIG. 16B. As can be seen clearly in FIG. 16B, the opposing beams define flexure voids 228 between the rotation constraint 226 and the proximal bushing 222 and between the rotation constraint 226 and the distal bushing 224. FIG. 17 illustrates an example of the rotation adapter receiver 216 installed in the handle of a minimally invasive surgical suturing device in order to support a rotation adapter 284, the features of which will be discussed later in this specification. The handle 126 of the suturing device may be molded to engage the opposing beams 218, 220 of the rotation adapter receiver 216 so that it is held in place.

Figure 18A:
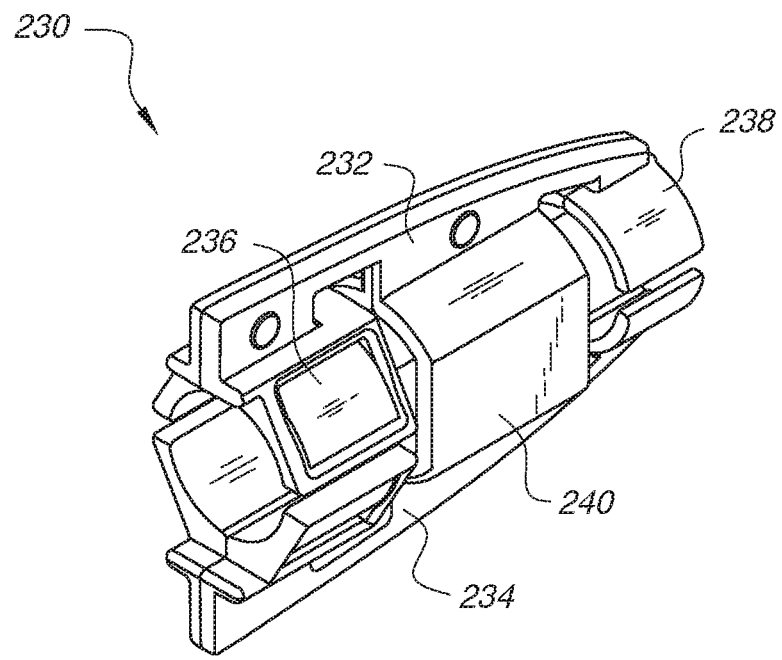
FIGS. 18A and 18B illustrate another embodiment of a rotation adapter receiver in assembled and disassembled forms, respectively.

FIG. 18A illustrates another embodiment of an assembled rotation adapter receiver 230. The rotation adapter receiver 230 has opposing beams 232, 234. A proximal bushing 236 is coupled between the opposing beams 232, 234. A distal bushing 238 is also coupled between the opposing beams 232, 234. In this embodiment, both the proximal and distal bushings 236, 238 are split bushings. The rotation adapter receiver 230 also has a rotation constraint 240 coupled between the opposing beams 232, 234 and positioned between the proximal and distal bushings 236, 238. In this embodiment, the rotation adapter receiver 230 of FIG. 18A is constructed from two identical parts. In other embodiments, the components which make up a rotation adapter receiver need not be identical, however, as mentioned previously, if the parts are identical, then the manufacturing process is simplified.

Figure 18B:
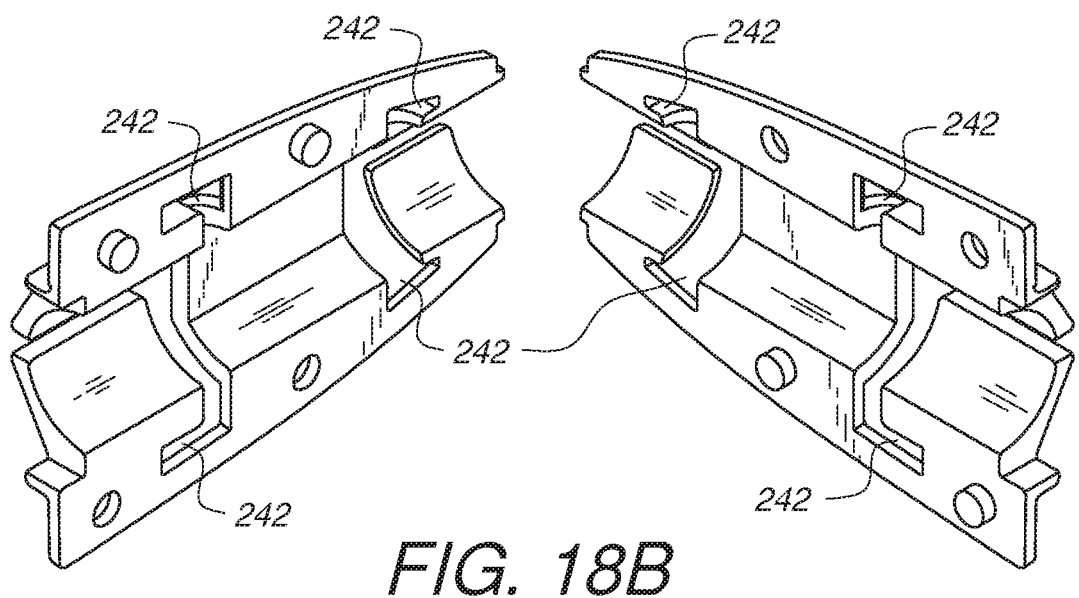
Figure 19:
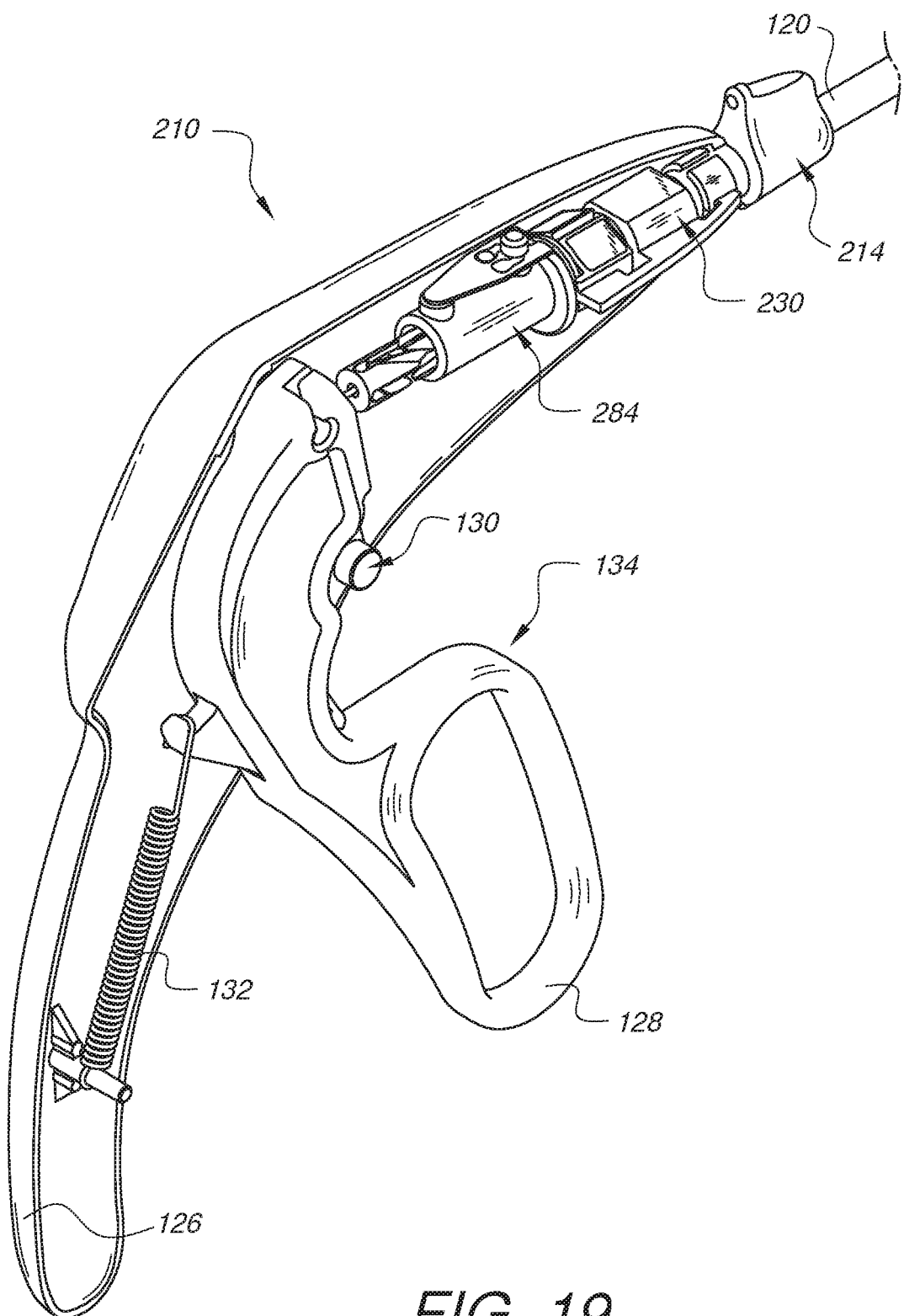
FIG. 19 is a partially exposed perspective view of another embodiment of a minimally invasive surgical suturing device having a rotation adapter supported by the rotation adapter receiver of FIG. 18A.

The identical parts which make up the rotation adapter receiver 230 are shown separated in FIG. 18A. As can be seen clearly in FIG. 18B, the opposing beams define flexure voids 242 between the rotation constraint 240 and the proximal bushing 236 and between the rotation constraint 240 and the distal bushing 238. FIG. 19 illustrates an example of the rotation adapter receiver 230 installed in the handle of a minimally invasive surgical suturing device in order to support a rotation adapter 284, the features of which will be discussed later in this specification. The handle 126 of the suturing device may be molded to engage the opposing beams 232, 234 of the rotation adapter receiver 230 so that it is held in place.

Figure 20A:
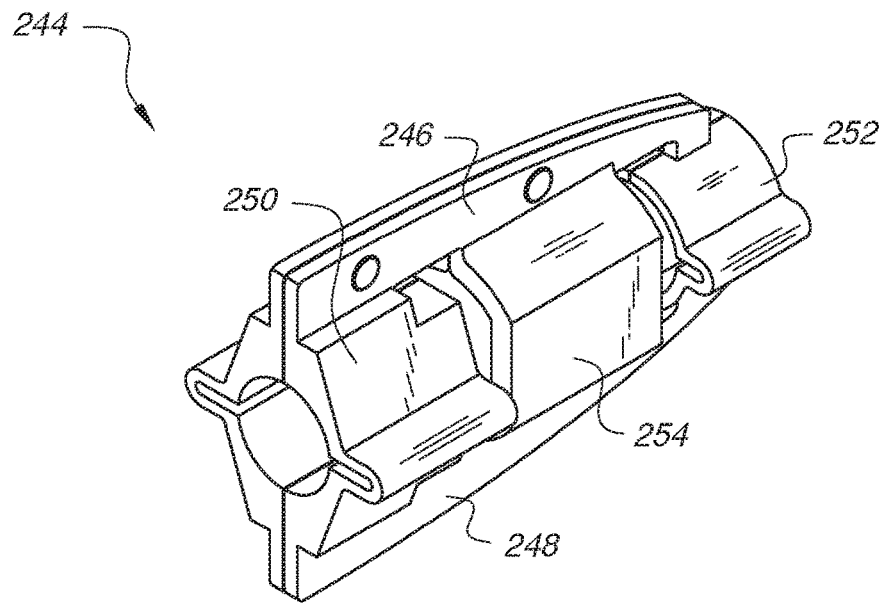
FIGS. 20A and 20B illustrate a further embodiment of a rotation adapter receiver in assembled and disassembled forms, respectively.

FIG. 20A illustrates another embodiment of an assembled rotation adapter receiver 244. The rotation adapter receiver 244 has opposing beams 246, 248. A proximal bushing 250 is coupled between the opposing beams 246, 248. A distal bushing 252 is also coupled between the opposing beams 246, 248. In this embodiment, both the proximal and distal bushings 250, 252 are clinch bushings. The rotation adapter receiver 244 also has a rotation constraint 254 coupled between the opposing beams 246, 248 and positioned between the proximal and distal bushings 250, 252. The rotation adapter receiver 244 of FIG. 20A is constructed from two identical parts. In other embodiments, the components which make up a rotation adapter receiver need not be identical, however, if the parts are identical, as mentioned previously, then the manufacturing process is simplified.

Figure 20B:
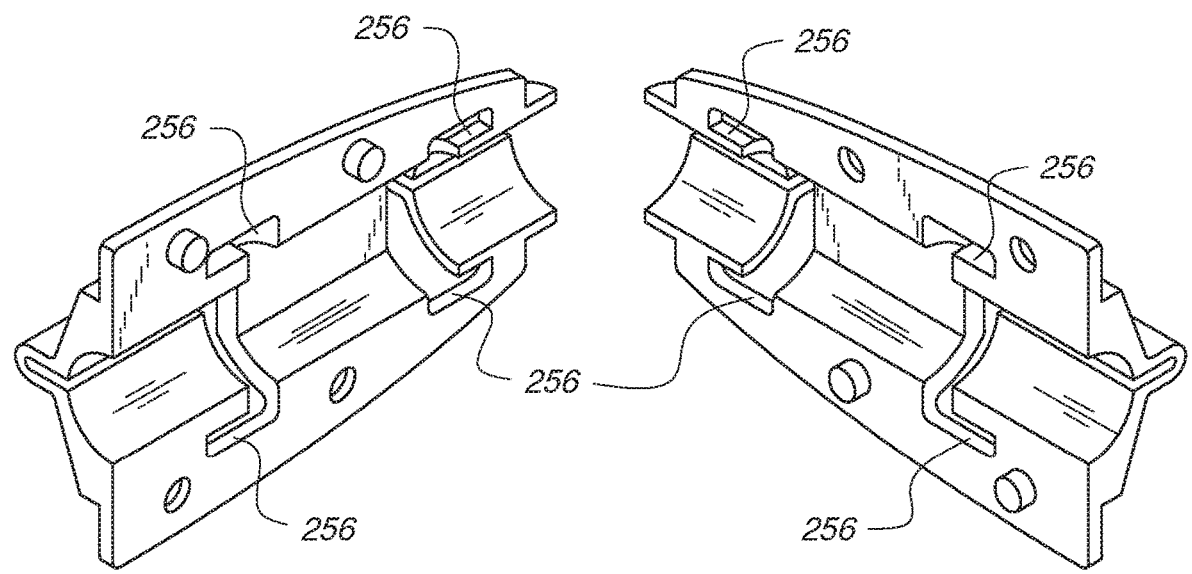
Figure 21:
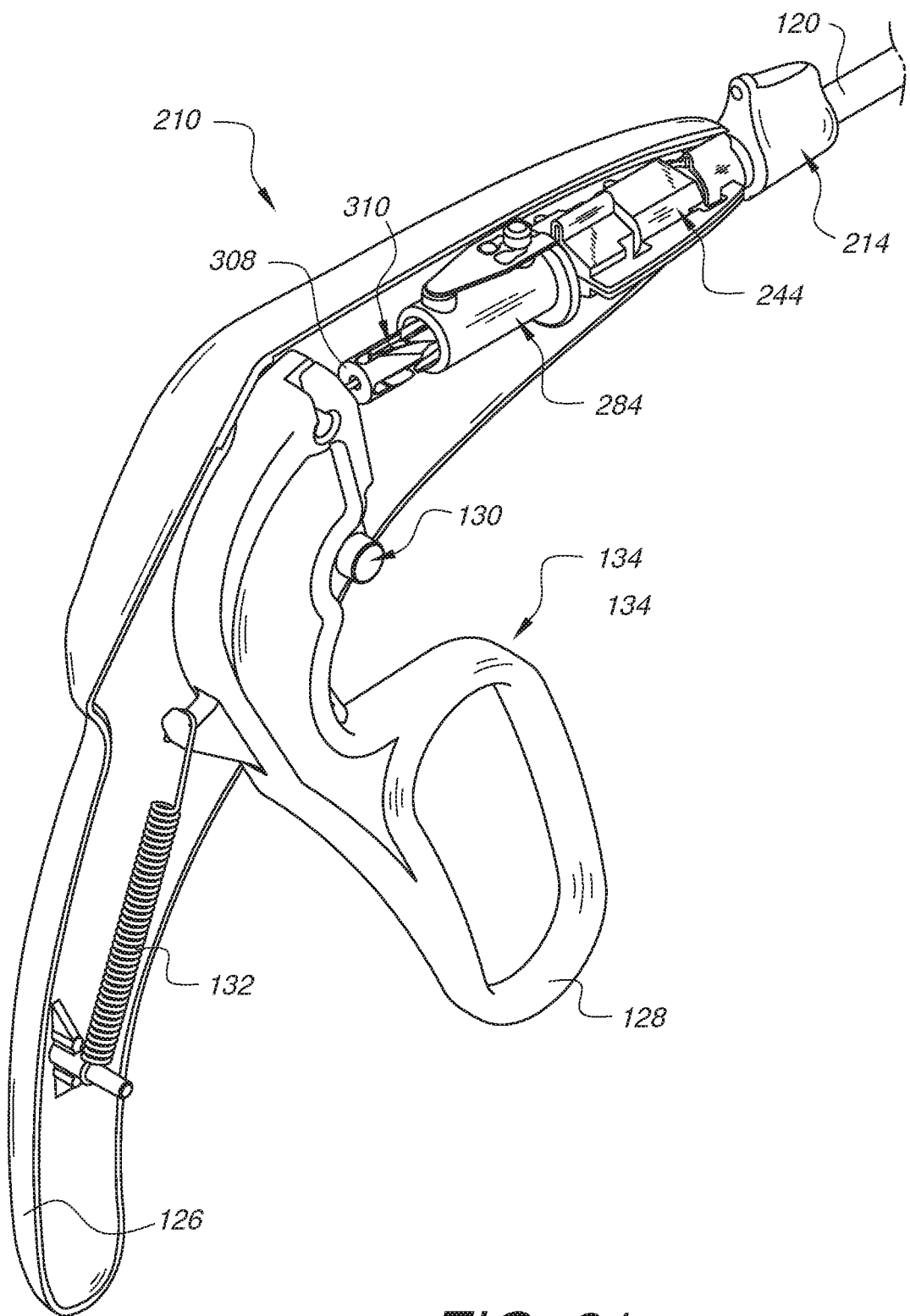
FIG. 21 is a partially exposed perspective view of a further embodiment of a minimally invasive surgical suturing device having a rotation adapter supported by the rotation adapter receiver of FIG. 20A.

The identical parts which make up the rotation adapter receiver 244 are shown separated in FIG. 20B. As can be seen clearly in FIG. 20B, the opposing beams define flexure voids 256 between the rotation constraint 254 and the proximal bushing 250 and between the rotation constraint 254 and the distal bushing 252. FIG. 21 illustrates an example of the rotation adapter receiver 244 installed in the handle of a minimally invasive surgical suturing device in order to support a rotation adapter 284, the features of which will be discussed later in this specification. The handle 126 of the suturing device may be molded to engage the opposing beams 246, 248 of the rotation adapter receiver 244 so that it is held in place.

FIGS. 22A and 22B illustrate a schematic cross-sectional view of a rotation constraint 258 (of a rotation adapter receiver) and the rotation index 260 (of a rotation adapter) in both a resting state and a transitory state between two resting positions, respectively. In the transitory state of FIG. 22B, the apex 262 between adjacent facets of the rotation index 260 causes the rotation constraint 258 to deform. The rotation constraint 258 should be constructed from a material which will endure this deformation while being able to transition back to its undeformed state when the rotation is completed.

As mentioned earlier, it has been found that it is advantageous to have a rotation adapter receiver which integrates bushings with a rotation constraint in a manner which relieves stress from the rotation constraint. FIG. 23 illustrates how one of the present embodiments and its equivalents accomplish this additional benefit. FIG. 23 is a cross-sectional perspective view of one embodiment of a rotation adapter receiver 230 with the rotation index 260 of a rotation adapter visible within the rotation constraint 240. Without being tied to one specific theory, modelling suggests that the deformation stress imparted into the rotation constraint 240 (the deformation stress being denoted with shading) is somewhat dissipated into the opposing beams 232, 234, and especially attenuated in the area of the beams near the flexure voids 242. This may enable a greater choice of materials than a design featuring a rotational constraint which is separate from bushings and/or which does not include one or more opposing beams.

Figure 24:
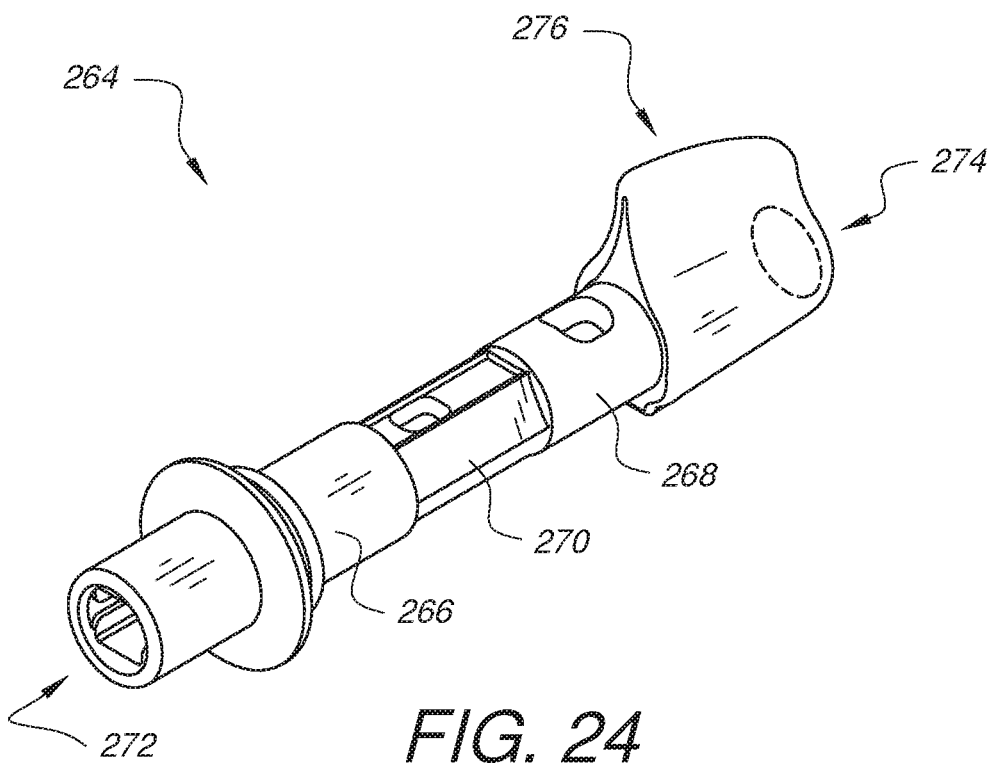
FIG. 24 illustrates one embodiment of a rotation adapter for use with a minimally invasive surgical apparatus for applying surgical knots.

As noted above, a rotation adapter can work in conjunction with a rotation adapter receiver. FIG. 24 illustrates one embodiment of a rotation adapter 264, in this case for use with a minimally invasive surgical apparatus for applying surgical knots. The rotation adapter 264 has a proximal journal 266 and a distal journal 268. The proximal journal 266 is configured to spin within a proximal bushing, while the distal journal 268 is configured to spin within a distal bushing. The rotation adapter 264 also has a rotation index 270 coupled between the proximal and distal journals 266, 268. The rotation adapter 264 further has an actuator input 272 (in this embodiment a keyed slot) and an effector output 274. This embodiment also has an effector direction indicator 276, which functions like the rotation knob discussed above.

Figure 25:
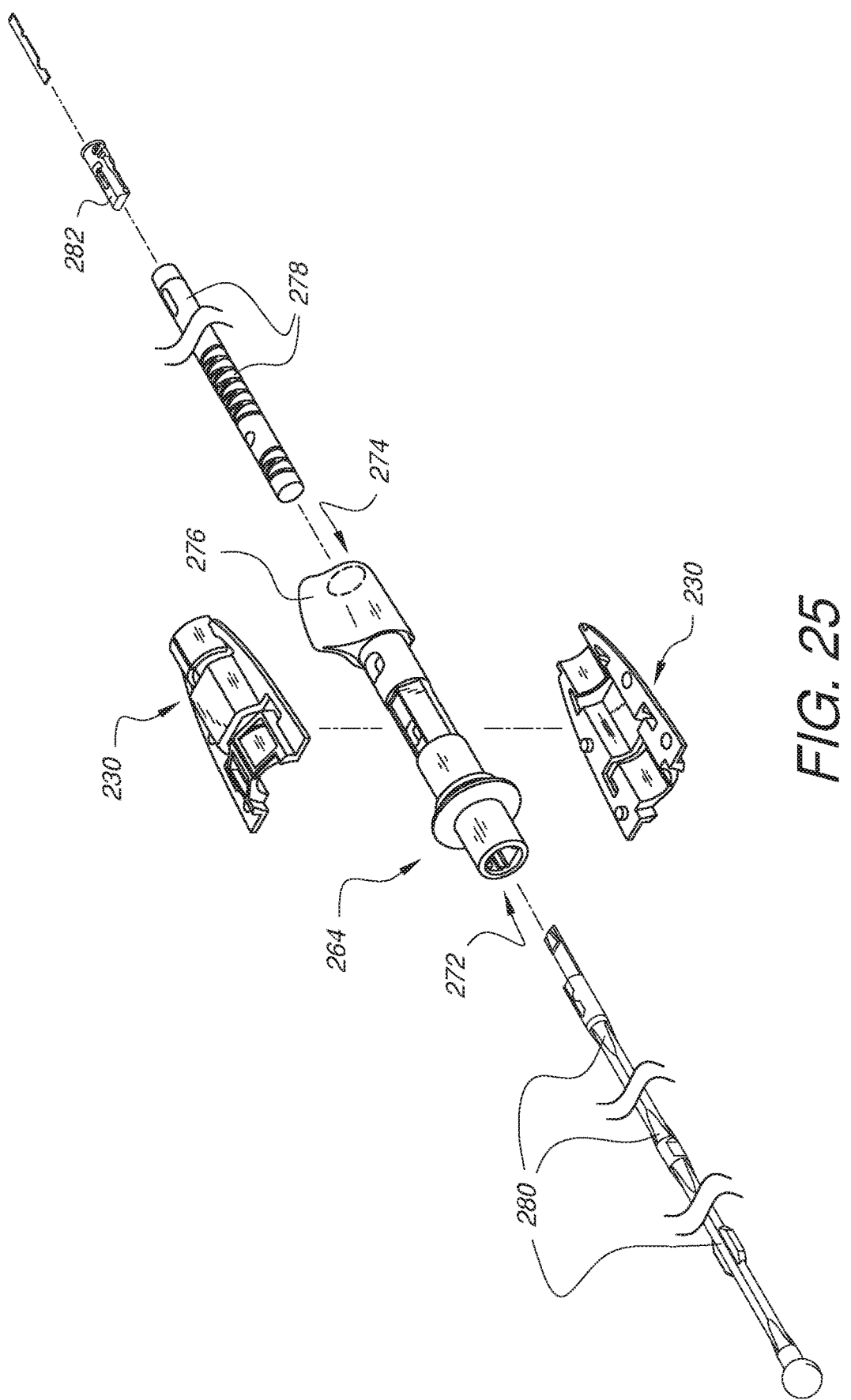
FIG. 25 is an exploded view of a portion of a minimally invasive surgical apparatus for applying surgical knots and having the rotation adapter of FIG. 24.

As illustrated in the exploded view of FIG. 25, a shaft 278 may be coupled to the effector output 274 of the rotation adapter 264. An actuator rod/pusher 280 may be inserted into the actuator input 272 of the rotation adapter 264. The pusher 280 may extend through the shaft 278 and into operational contact with a hammer/anvil 282 for crimping mechanical knots. In this embodiment, the actuator input 272 is keyed so that rotation of the effector direction indicator 276 not only rotates the shaft 278, but also the actuator rod/pusher 280. The keyed actuator input 272 allows rotation of the rotation adapter 264 to rotate the actuator rod/pusher 280 while the actuator rod/pusher 280 is free to slide axially within the rotation adapter. The rotation adapter 264 fits within the halves of the rotation adapter receiver 230.

Figure 26:
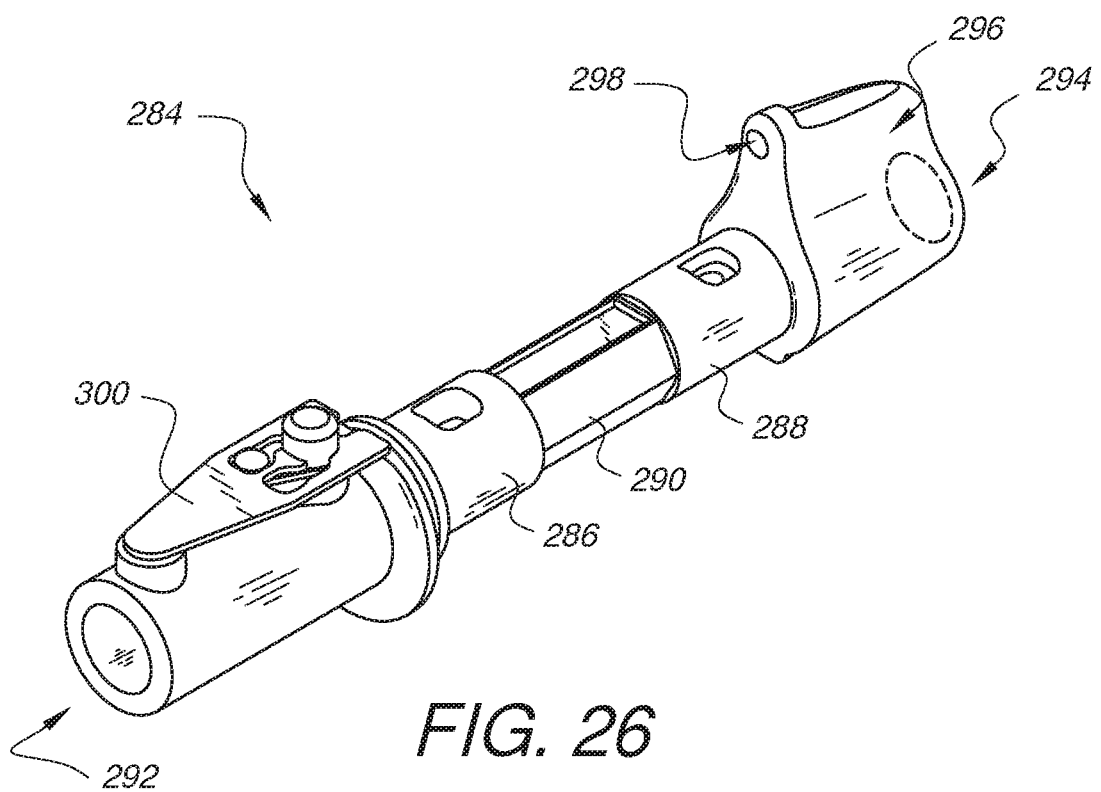
FIG. 26 illustrates one embodiment of a rotation adapter for use with a minimally invasive surgical suturing device.

FIG. 26 illustrates another embodiment of a rotation adapter 284, in this case, for use with a minimally invasive surgical apparatus for suture stitching. The rotation adapter 284 has a proximal journal 286 and a distal journal 288. The proximal journal 286 is configured to spin within a proximal bushing, while the distal journal 288 is configured to spin within a distal bushing. The rotation adapter 284 also has a rotation index 290 coupled between the proximal and distal journals 286, 288. The rotation adapter 264 further has an actuator input 292 (in this embodiment for receiving a needle twisting barrel) and an effector output 294. This embodiment also has an effector direction indicator 296. The effector direction indicator 296 functions like the rotation knob and the direction indicator 276 discussed above, however this direction indicator 296 also includes a suture management feature 298 through which a suture end may be threaded so that the suture follows the rotation of the end effector from which it comes, thereby helping to prevent suture tangling as the end effector is rotated. The actuator input 292 also includes a cam spring 300 that will be discussed in more detail with the following figure.

Figure 27:
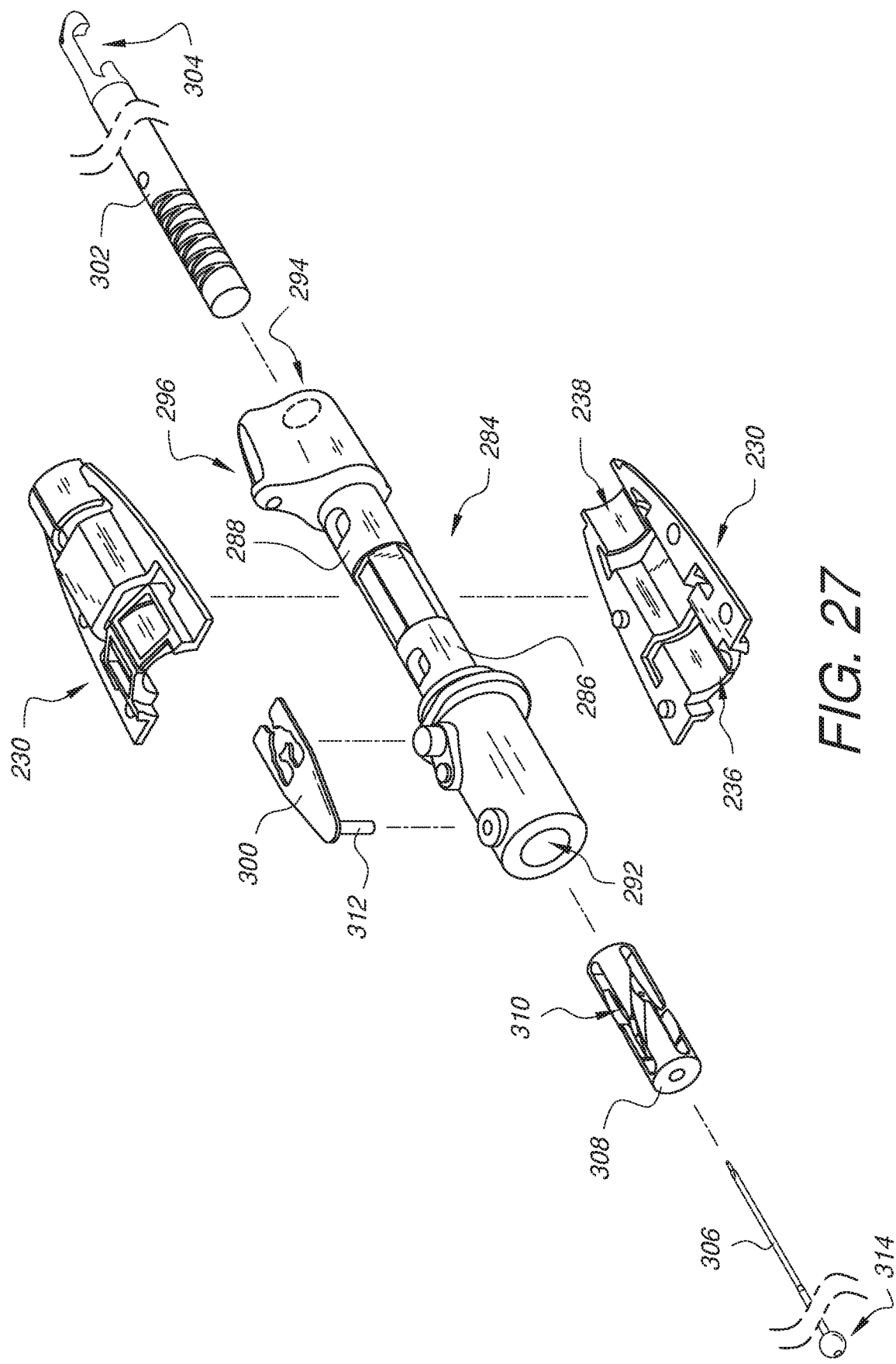
FIG. 27 is an exploded view of a portion of a minimally invasive surgical suturing device and having the rotation adapter of FIG. 26.

As illustrated in the exploded view of FIG. 27, a shaft 302 may be coupled to the effector output 294 of the rotation adapter 284. A suturing tip 304 with a tissue bite area and a ferrule holder (known to those skilled in the art) may be located at the distal end of the shaft 302. A needle 306 passes through and is coupled to a needle twisting barrel 308. The barrel 308 has cam paths 310 which are engaged by a cam 312 biased against the barrel 308 by a cam spring 300 when the barrel 308 is placed into the actuator input 292 of the rotation adapter 284. An actuator (not shown) coupled to the proximal end 314 of the needle 306 moves the barrel axially back and forth within the actuator input 292. The interference of the cam 312 with the cam path 310 causes the needle to rotate 90 degrees every time the needle is pulled back in a proximal direction. This rotation of the needle facilitates a running stitch as is known to those skilled in the art, and as will be further explained below. The proximal and distal journals 286, 288 ride within the proximal and distal bushings 236, 238 of the rotation adapter receiver 230. When the effector direction indicator 296 is rotated, the rotation adapter rotates, causing the coupled shaft 302 also to rotate. The engagement of the cam 312 with the sides of the cam path 310 of the barrel 308 also causes the needle barrel 308 to correspondingly rotate. Thus, the relationship of the needle 306 to the suturing tip 304 is preserved, even when the direction indicator 296 is used to rotate the shaft 302 and the device tip 304.

Figure 28:
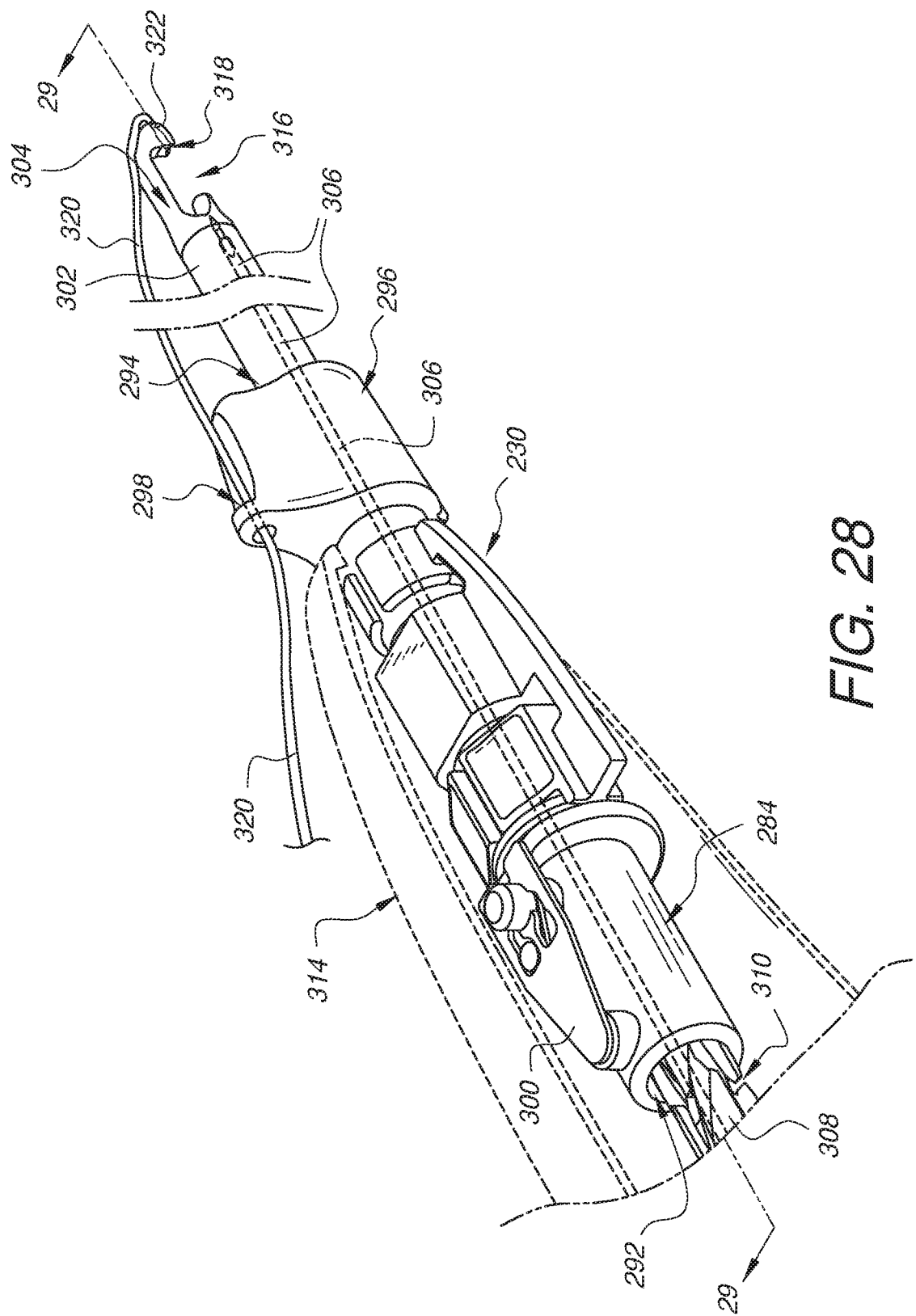
FIG. 28 is an assembled perspective view of the rotation adapter receiver 230 and the rotation adapter 284 from FIG. 27.

FIG. 28 is an assembled perspective view of the rotation adapter receiver 230 and the rotation adapter 284 from FIG. 27. shown schematically as part of a minimally invasive surgical suturing device 314. As mentioned previously, the suturing device 314 may have a suturing tip 304 which defines a tissue bite area 316. The tip 304 may also define a ferrule receiver 318. A suture 320 with a ferrule 322 attached to a first end of the suture may be used in conjunction with the suturing device 314. The ferrule 322 may be loaded into the ferrule holder 318, and an opposite end of the suture 320 may be threaded through the suture management feature 298 on the direction indicator 296.

FIGS. 29A-29G illustrate how the suturing device is used to advance the needle 306 through tissue and across the tissue bite area 316 to pick up the ferrule 322 so that the ferrule (and its attached suture) may be pulled back through the tissue and then the process repeated. FIGS. 29A-29G are partial cross-sectional side views of the suturing device of FIG. 28 taken along line 29-29.

Figure 29A:
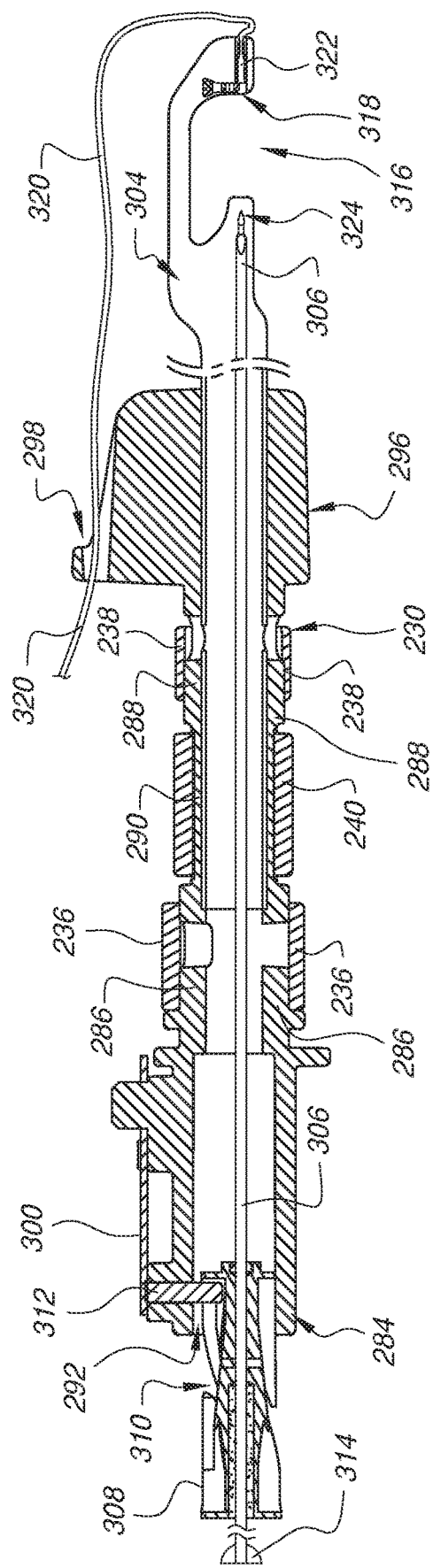
FIGS. 29A-29G illustrate an example of a suturing device having a rotation adapter being used to place a suture stitch into tissue.

As shown in FIG. 29A, the needle 306 passes through and is coupled to the needle twisting barrel 308. The barrel 308 has cam paths 310 which are engaged by cam 312. Cam 312 is biased against the barrel 308 by cam spring 300. A proximal end 314 of the needle 306 is coupled to an actuator (not shown). The actuator is capable of selectively moving the needle 306 (and therefore, also the barrel 308 to which it is attached) axially back and forth within the actuator input 292 if the rotation adapter 284. As illustrated in FIG. 29A, the needle 306 is in a retracted position where the tip 324 of the needle 306 is housed within the suturing tip 304 and has not passed through the tissue bite area 316. The ferrule 322, coupled to the suture 320, is loaded within the ferrule holder 318 on the distal side of the tissue bite area 316 in the suturing tip 304.

Figure 29B:
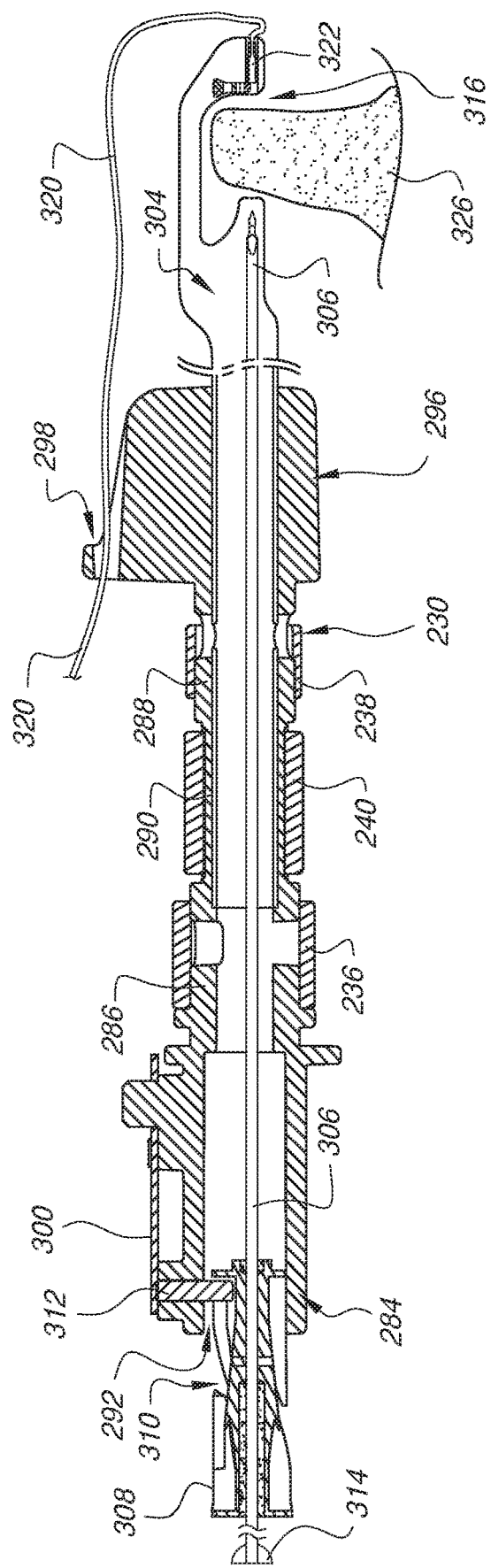
Figure 29C:
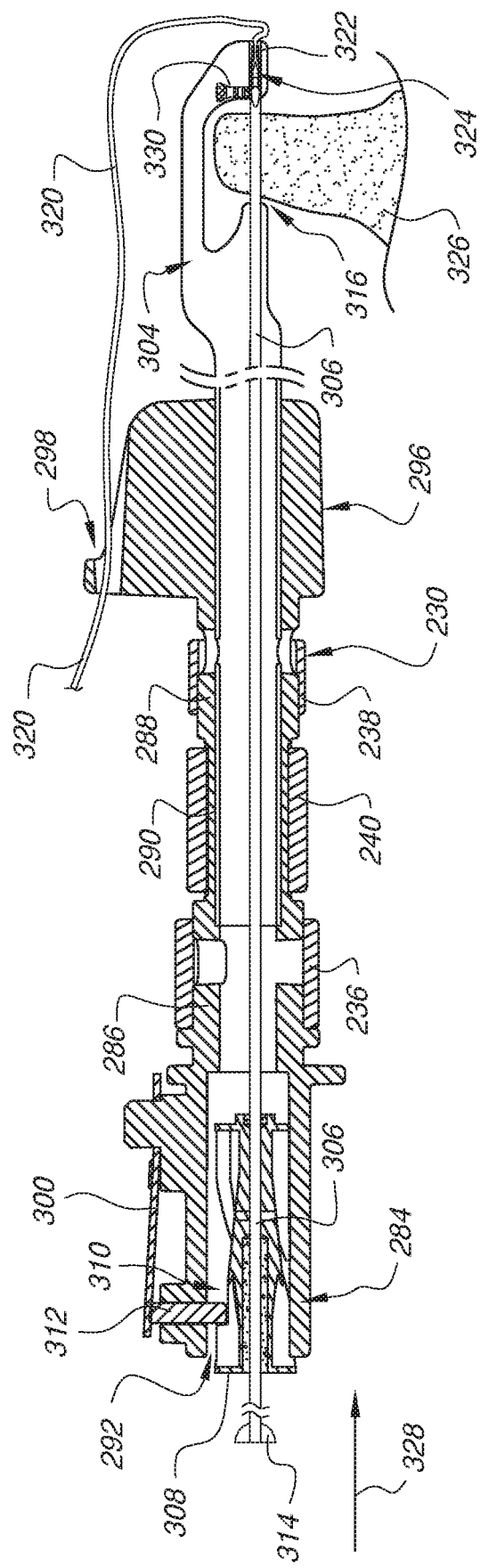

As illustrated in FIG. 29B, the device may be positioned so that tissue 326 is within the tissue bite area 316. As shown in FIG. 29C, the actuator (not shown) may move the needle 306 in a distal direction 328, such that the needle tip 324 passes through the tissue 326 in the tissue bite area 316, past a spring 330 that rides on the needle 306, and into an interference fit with the ferrule 322.

Figure 29D:
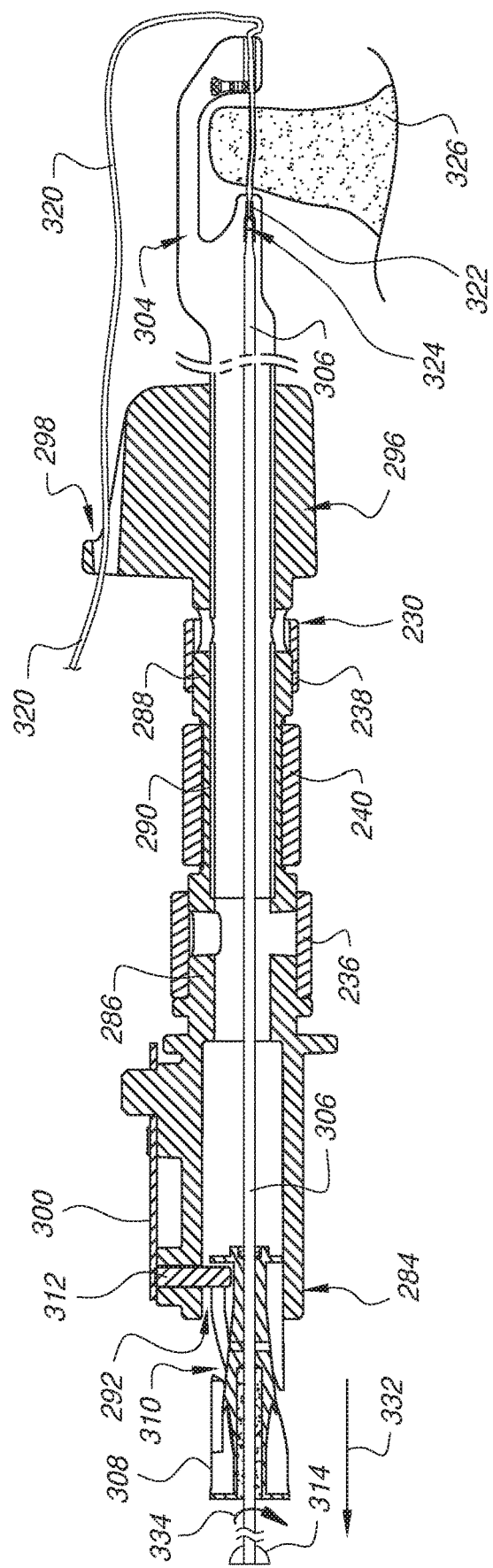

As illustrated in FIG. 29D, the actuator (not shown) may move the needle 306 in a proximal direction 332, such that the needle tip 324, the ferrule 322 which is coupled to it, and a portion of the suture 320 coupled to the ferrule 322 pass back through the tissue 326. As this proximal movement 332 of the needle 306 begins, the needle tip 324 is oriented as shown in FIG. 29C. In this orientation, there is not enough gap between the outer surface of the needle 306 and the ferrule 322 to allow the spring 330 to remove the ferrule 322 from the needle 306. Recall, however, that the barrel 308 is coupled to the needle 306. The barrel 308 has cam paths 310, and the rotation adapter 284 has a spring 300 which biases a cam 312 against the barrel 308 so that the cam 312 rides within the cam paths. The cam paths 310 are configured so that the barrel 308 (and therefore, the needle 306) does not rotate when the needle is moved in a distal direction. However, when the needle is moved proximally 332 as shown in FIG. 29D, the interference between the cam 312 and the cam paths 310 cause the barrel 308 (and therefore the needle 306) to rotate 334 ninety degrees to the position shown in FIG. 29D. The needle tip 324 has a more tapered profile where it mates with the ferrule 322 as shown in the view of FIG. 29D.

Figure 29E:
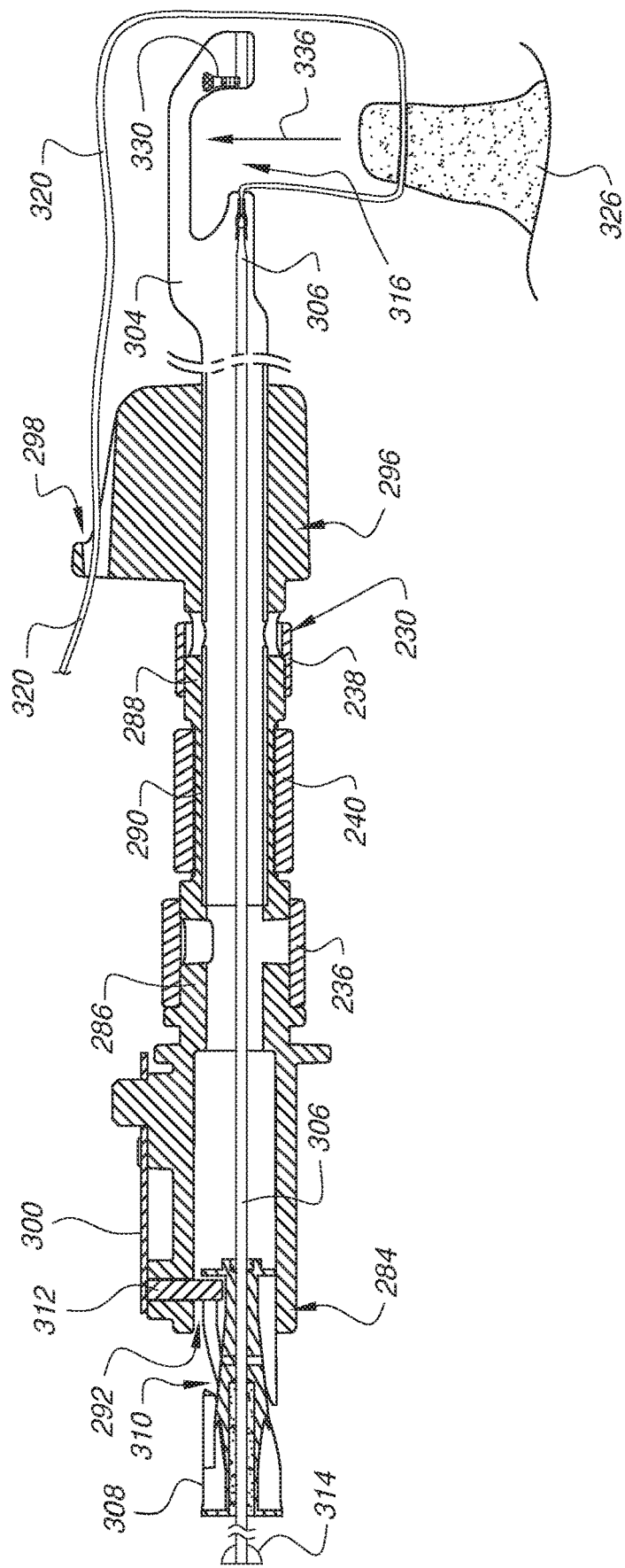
Figure 29F:
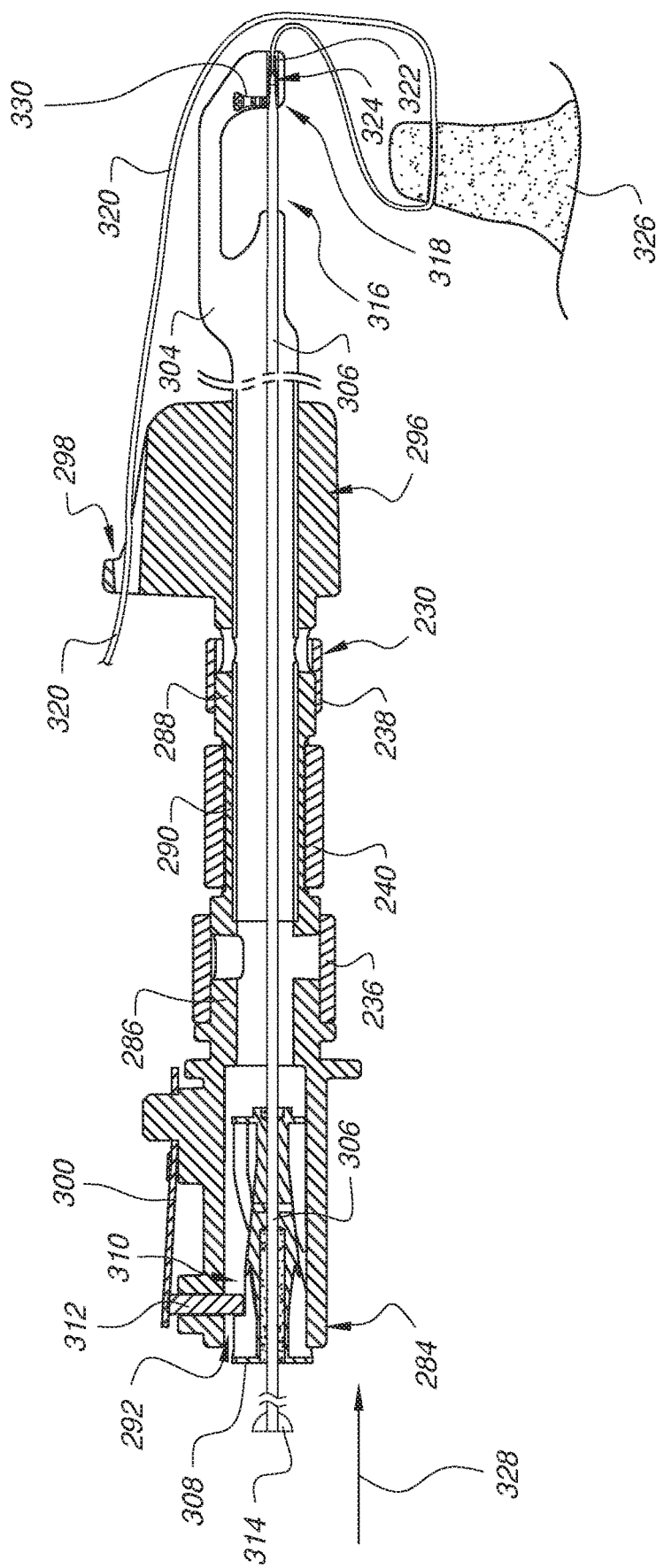
Figure 29G:
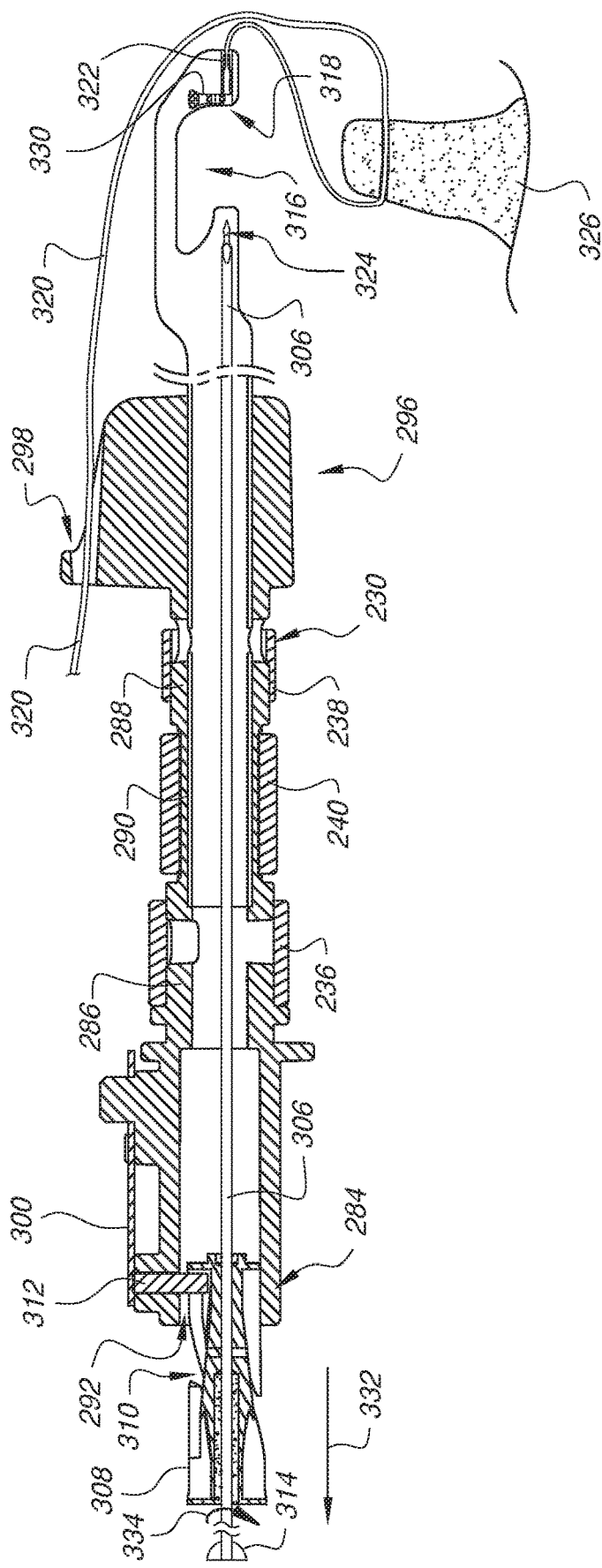

As illustrated in FIG. 29E, the suturing device may be lifted 336 so the tissue 326 is no longer in the tissue bite area 316. As illustrated in FIG. 29F, the needle 306 may be moved in a distal direction 328 so that the needle tip 324 passes through the tissue bite area and past the spring 330 that rides on the needle 306 such that the ferrule 322 is positioned again within the ferrule holder 318. Since the needle tip 324 offers a longer taper to the spring 330 in the orientation of FIG. 29F, the spring 330 pushes the ferrule 322 off of the needle tip 324 as the needle 306 is moved in a proximal direction 332 as shown in FIG. 29G. As shown in FIG. 29G, the cam 312 has again caused barrel 308 (and therefore needle 306) to rotate 334 ninety degrees as the needle 306/barrel 308 are moved proximally. The cam paths 110 are configured so that the rotation occurs after the ferrule 322 has been stripped from the needle tip 324. The device of FIG. 29G is now in the same configuration as that of FIG. 29A, and the process of FIGS. 29A-29G may be repeated as desired to place multiple stitches of the suture 320.

In the embodiments discussed herein previously, it has been mentioned that some embodiments of a surgical suturing device having a rotation adapter may include a suture management feature 298 as part of the direction indicator 296. Such a direction indicator 296 is shown on a sample surgical suturing device 338 in FIG. 30A. In this example, the surgical suturing device 338 has two needles (not visible in this view) which can traverse the tissue bite area 340 in a manner similar to that understood by those skilled in the art. First and second ferrules (not visible in this view) are coupled to the ends of a suture 342. The ferrules are held within ferrule holders 344, and the suture 342 can be wrapped around the back of the distal tip 346. In this embodiment, the shaft 348 also has a suture management feature 350 through which the suture 342 may be threaded. If the suture is long enough, the suture 342 may also be threaded through the suture management feature 298 on the direction indicator.

Figure 30A:
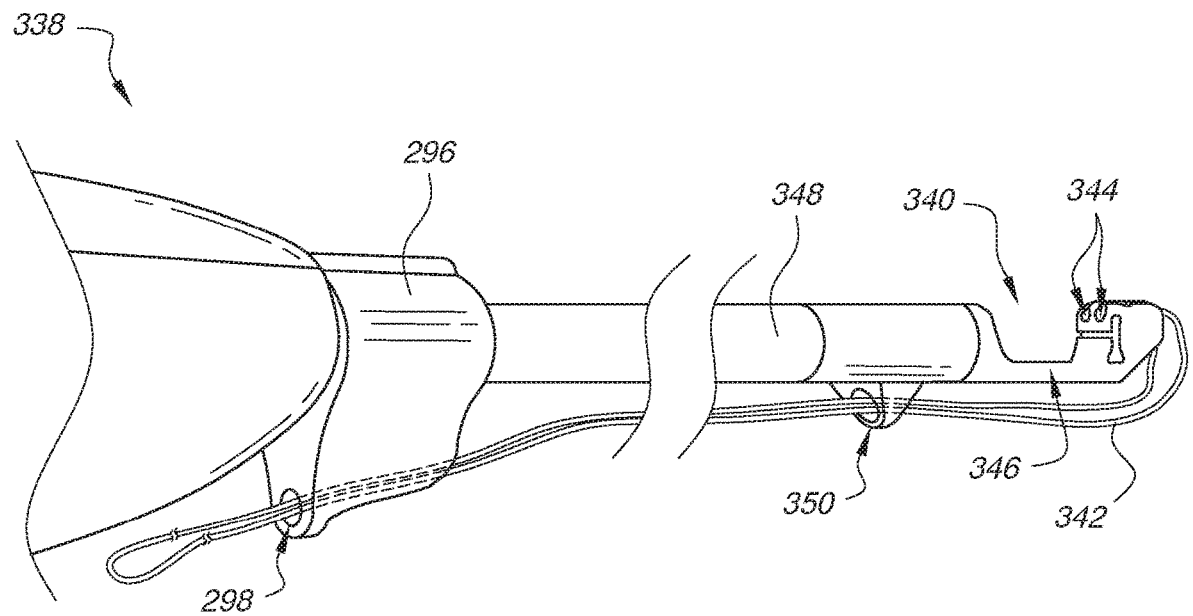
FIGS. 30A-30B illustrate different embodiments of suture management features on a minimally invasive surgical suturing device having a rotation adapter.
Figure 30B:
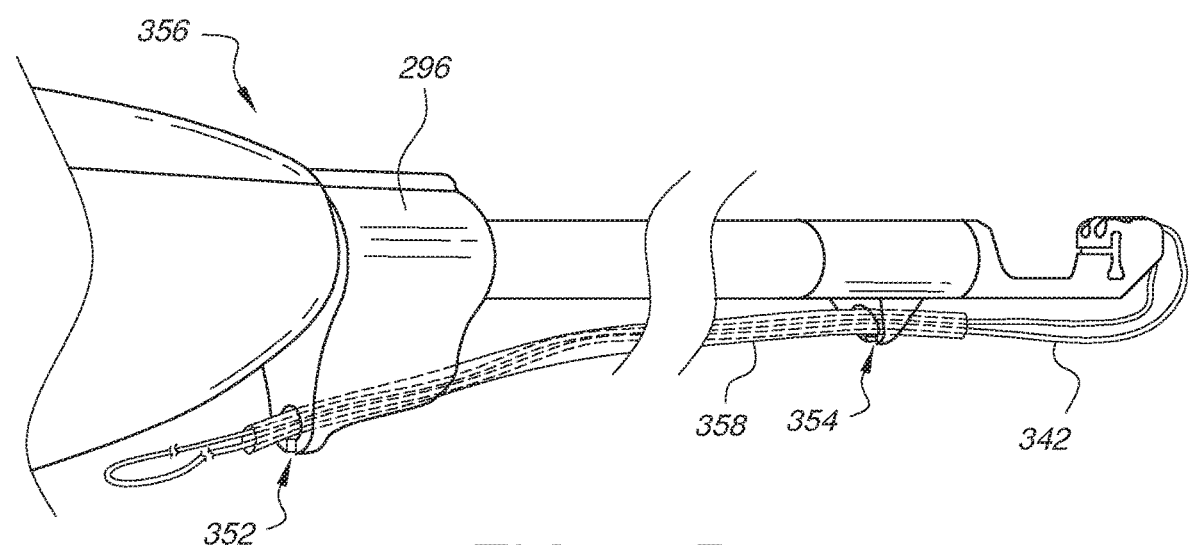

In the embodiment of FIG. 30A, the suture management features 298, 350 are holes through which the suture 342 must be threaded. In other embodiments, the suture management features may have other characteristics. For example, in the embodiment of FIG. 30B, the suture management features 352 and 354 of another surgical suturing device 356 are slotted to be able to receive a tube 358 in which the suture 342 has been pre-loaded. This allows the tube 358 to be snapped quickly into the suture management features 352, 354 rather than having to take the time to thread the suture.

Figure 31:
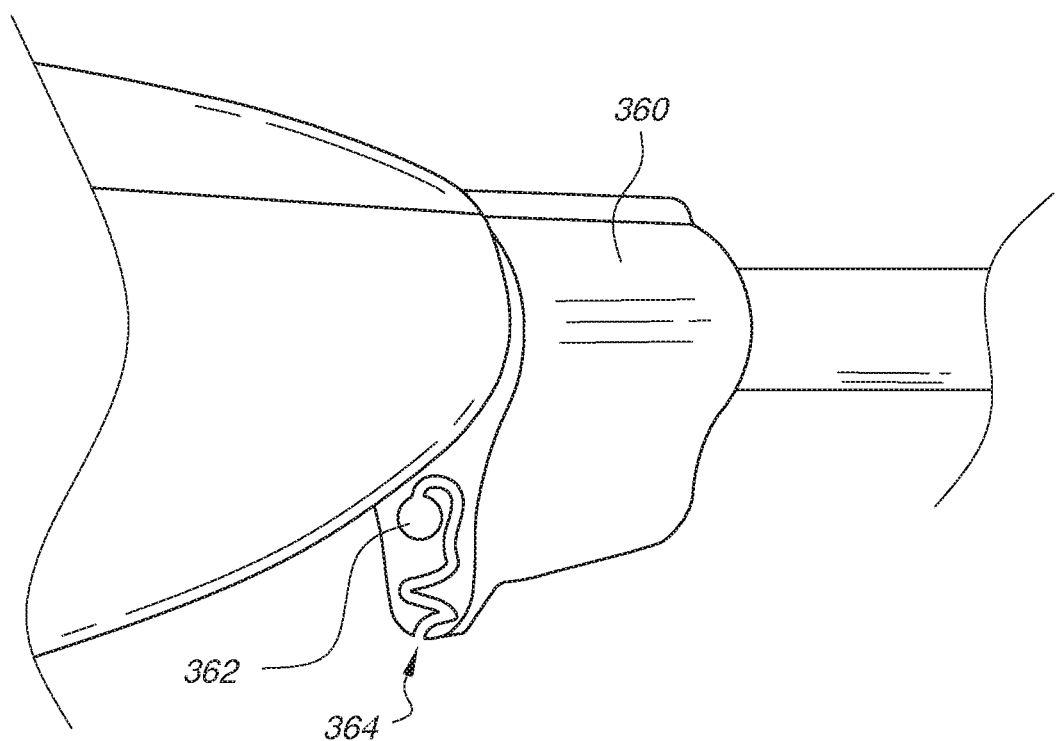
FIG. 31 illustrates a further embodiment of a suture management feature for a direction indicator of a rotation adapter.

FIG. 31 illustrates another embodiment of a direction indicator 360. This direction indicator 360 has yet another suture management feature 362. In this embodiment, a tortuous path 364 leads to the suture management feature so that a suture may more easily be worked into the suture management feature 362 than simple threading. Any middle portion of a suture can be placed into the tortuous path 364 and worked back and forth along the path until the suture reaches the suture management feature 362.

Various advantages of a rotation adapter and rotation adapter receiver have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. An assembly for a minimally invasive surgical apparatus, the assembly comprising:
   a rotation adapter comprising:
      a proximal journal;
      a distal journal;
      a bore extending between a distal end of the rotation adapter and a proximal end of the rotation adapter;
      a rotation index coupled between the proximal and distal journals, wherein the rotation index further comprises a plurality of facets and an apex between two adjacent facets;
      an actuator input disposed adjacent to the proximal end of the rotation adapter;
      an elongated cam spring, wherein a first end of the cam spring is secured to a first portion of the rotation adapter and a second end of the cam spring is adapted to displace relative to the first end of the cam spring, wherein a cam extends from the second end of the cam spring such that the cam is displaceably received into an aperture disposed through a second portion of the rotation adapter, and wherein an end portion of the cam is disposed within the bore; and
      an effector output disposed adjacent to the distal end of the rotation adapter; and
   a rotation adapter receiver comprising:
      a rotation constraint having one or more surfaces that define a constraint passage that receives the rotation index such that the rotation adapter is configured to rotate relative to the rotation constraint, wherein as the rotation adapter rotates within the constraint passage, the apex between the two adjacent facets of the rotation index contacts a corresponding portion of the rotation constraint and deforms the corresponding portion of the rotation constraint.

2. The assembly of claim 1, the rotation adapter further comprising an effector direction indicator.

3. The assembly of claim 2, wherein the effector direction indicator comprises a suture management feature.

4. The assembly of claim 1, wherein the effector output is configured to engage a pusher for a mechanical knot crimper.

5. The assembly of claim 1, wherein the effector output is configured to engage a needle.

6. The assembly of claim 1, further comprising:
   a barrel disposed in a portion of the bore of the rotation adapter, the barrel being displaceable along a bore axis that extends along the bore, the barrel having at least one cam path that extends along the barrel, wherein the end portion of the cam is received into a portion of the cam path such that as the cam path displaces along the bore axis, the end portion of the cam engages the portion of the cam path to rotate the barrel about the bore axis.

7. The assembly of claim 1, further comprising:
   a needle that extends through the barrel along the bore axis, wherein the needle is fixedly coupled to the barrel.

8. The assembly of claim 1, wherein the aperture disposed through the second portion of the rotation adapter is adjacent to the actuator input of the rotation adapter.

9. The assembly of claim 1, the rotation adapter receiver further comprising:
   a proximal bushing disposed proximally to the rotation constraint; and
   a distal bushing disposed distally to the rotation constraint, wherein the proximal journal of the rotation adapter rides within the proximal bushing and the distal journal of the rotation adapter rides within the distal bushing.

* * * * *